United States Patent
De Naeyer et al.

(10) Patent No.: US 10,806,862 B2
(45) Date of Patent: Oct. 20, 2020

(54) DEVICE AND METHOD FOR APPLYING A COMPOSITION ON THE SKIN OR SKIN LAYERS

(71) Applicant: Versailles B.V., Diemen (NL)

(72) Inventors: An De Naeyer, Kortrijk (BE); Mark Berkhout, Diemen (NL)

(73) Assignee: VERSAILLES B.V., Diemen (NL)

( * ) Notice: Subject to any disclaimer, the term of this patent is extended or adjusted under 35 U.S.C. 154(b) by 304 days.

(21) Appl. No.: 15/553,392

(22) PCT Filed: Feb. 25, 2016

(86) PCT No.: PCT/IB2016/051032
§ 371 (c)(1),
(2) Date: Aug. 25, 2017

(87) PCT Pub. No.: WO2016/135665
PCT Pub. Date: Sep. 1, 2016

(65) Prior Publication Data
US 2018/0126078 A1 May 10, 2018

(30) Foreign Application Priority Data
Feb. 27, 2015 (NL) .................................. 2014370

(51) Int. Cl.
*A61M 5/30* (2006.01)
*A61M 5/24* (2006.01)
*A61M 5/20* (2006.01)

(52) U.S. Cl.
CPC ................ *A61M 5/30* (2013.01); *A61M 5/24* (2013.01); *A61M 5/3007* (2013.01); *A61M 2005/2073* (2013.01); *A61M 2205/583* (2013.01); *A61M 2205/584* (2013.01)

(58) Field of Classification Search
CPC ........ A61M 5/30; A61M 5/24; A61M 5/3007; A61M 2005/2073
See application file for complete search history.

(56) References Cited

U.S. PATENT DOCUMENTS

| 5,026,343 A | * | 6/1991 | Holzer | A61M 5/30 |
| | | | | 604/135 |
| 6,053,890 A | * | 4/2000 | Moreau Defarges | A61M 5/30 |
| | | | | 604/232 |

OTHER PUBLICATIONS

International Search Report and Written Opinion issued in International Patent Application No. PCT/IB2016/051032 dated Jun. 14, 2016.

* cited by examiner

*Primary Examiner* — Rebecca E Eisenberg
*Assistant Examiner* — Anh Bui
(74) *Attorney, Agent, or Firm* — Leason Ellis LLP

(57) ABSTRACT

The present Invention relates to a kit for applying a liquid composition on or in the skin, comprising an injection device and one or more cartridges, provided with a container appropriate for receiving a liquid composition, in which the injection device is provided with means for receiving a cartridges, characterized in that the container is provided with a movable body. The cartridge is provided with a peripheral edge, that allows the safe removal of a used cartridge out of the device, In a second aspect, the invention relates to a method for applying a liquid composition onto the skin.

18 Claims, 24 Drawing Sheets section A - A

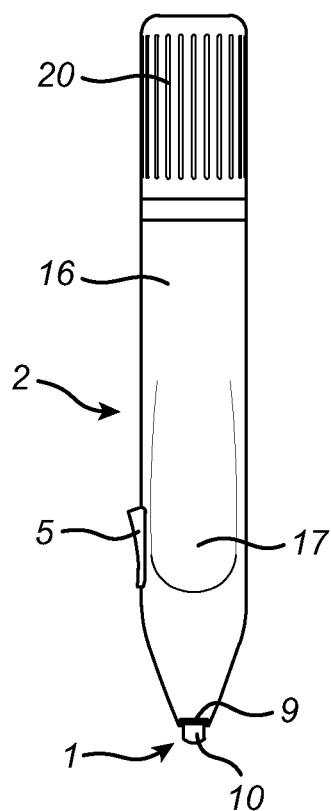
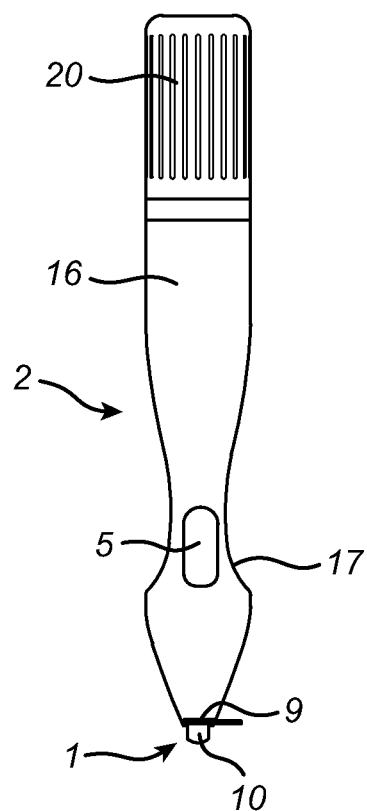
Fig. 1a  Fig. 1b
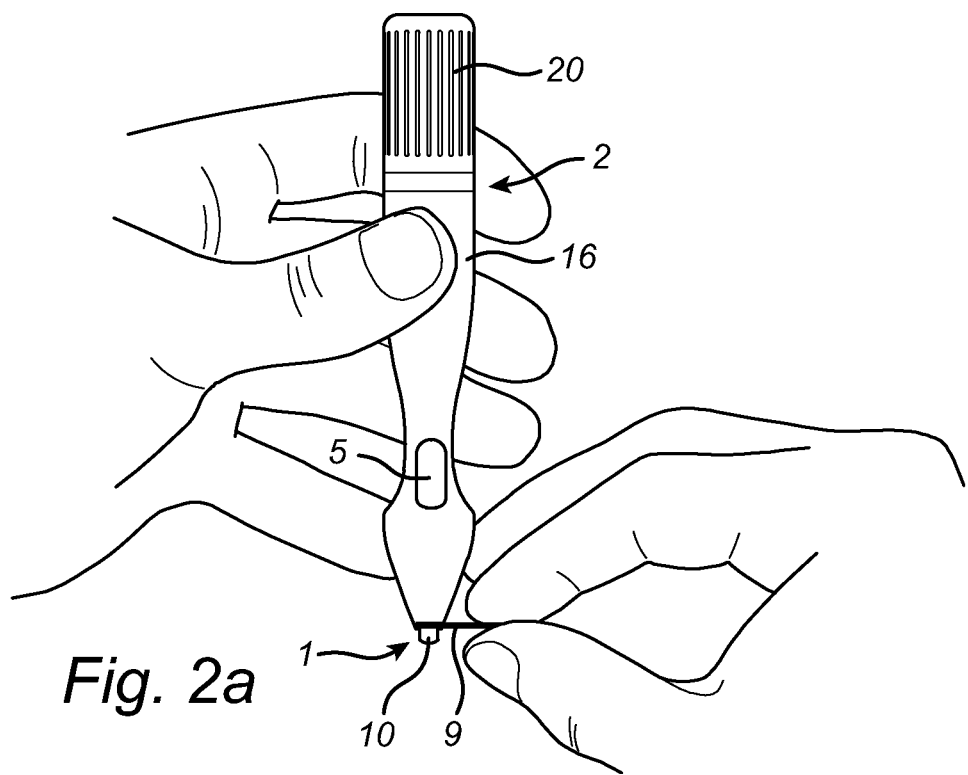
Fig. 2a

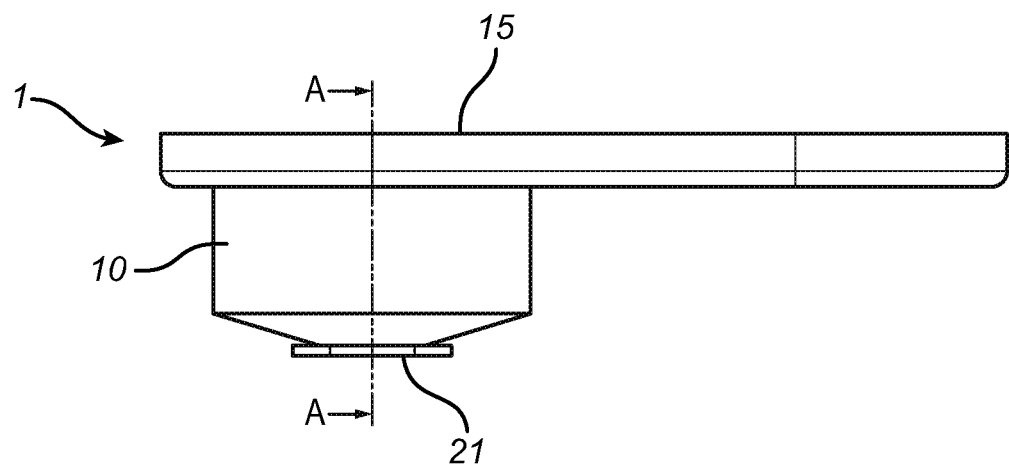
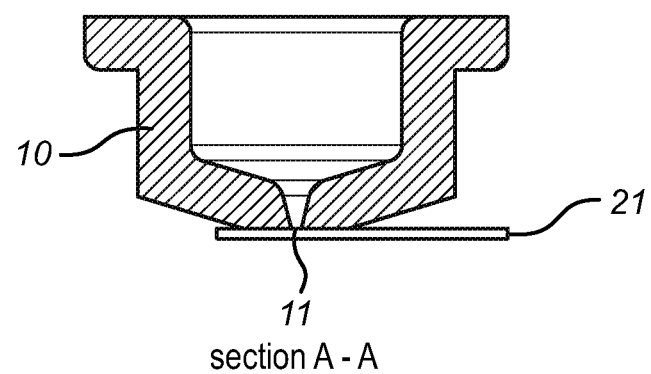
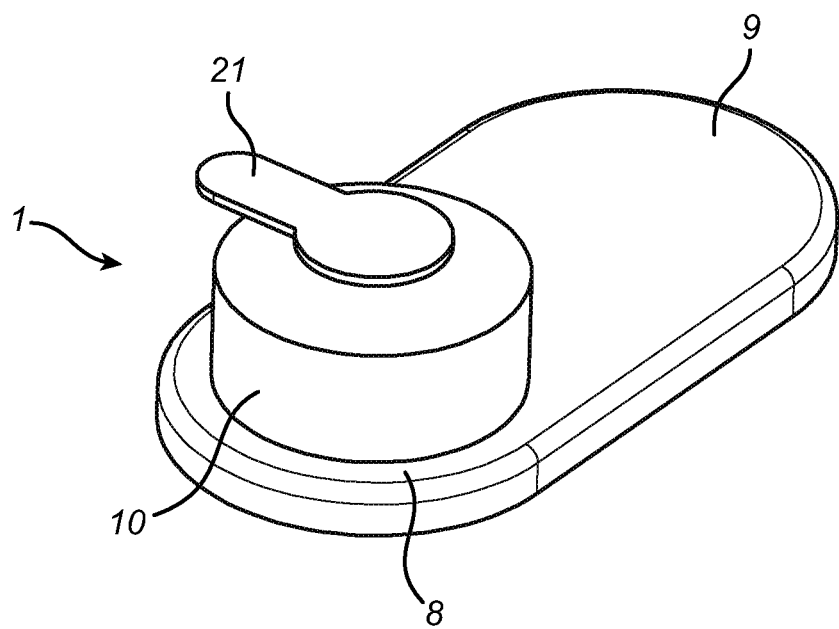
Fig. 3d

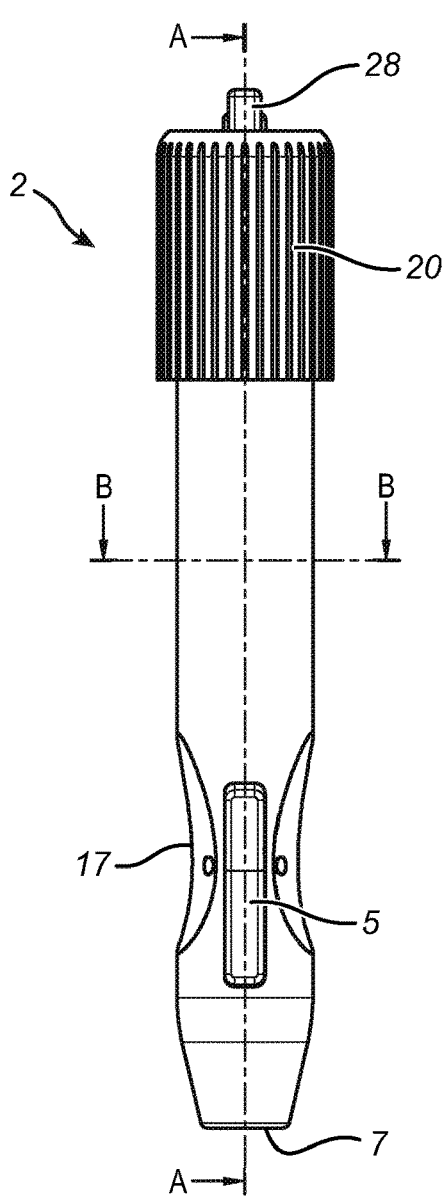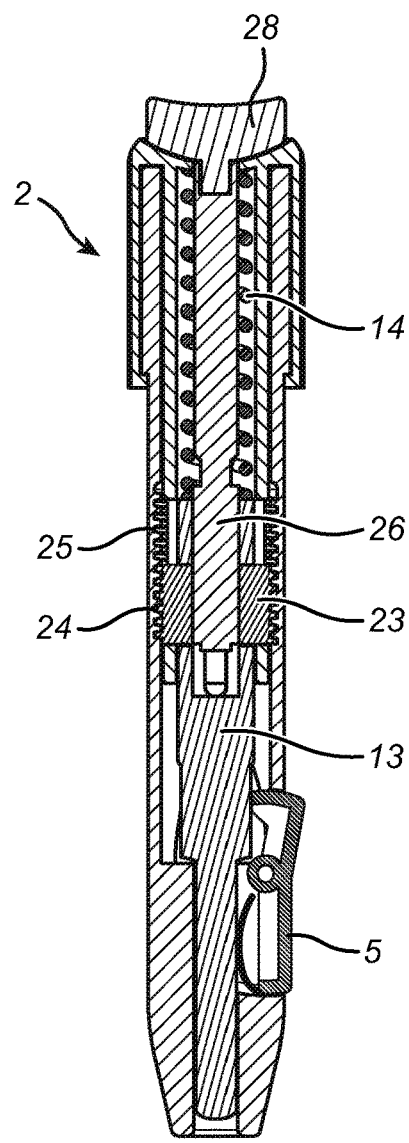
*Fig. 7a*  *Fig. 7b*
section A - A
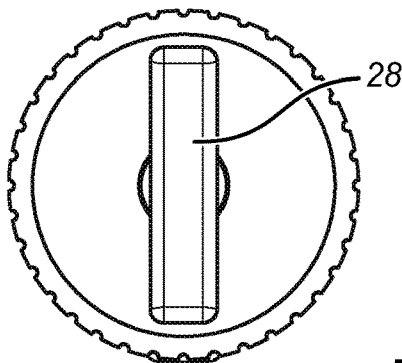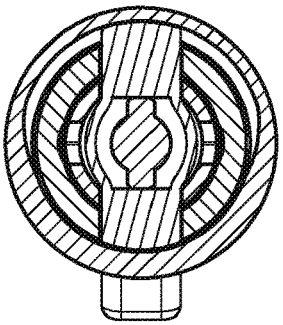
*Fig. 7c*  section B - B section A - A section B - B section A - A section B - B section D - D

DEVICE AND METHOD FOR APPLYING A COMPOSITION ON THE SKIN OR SKIN LAYERS

CROSS-REFERENCE TO RELATED APPLICATIONS

This application is a national stage application under 35 U.S.C. § 371 of International Patent Application No. PCT/IB2016/051032, filed Feb. 25, 2016 and published Sep. 1, 2016 as International Publication Number WO 2016/135665, which claims priority and benefit of The Netherlands Patent Application No. NL2014370, filed on Feb. 27, 2015, titled "DEVICE AND METHOD FOR APPLYING A COMPOSITION ON THE SKIN OR SKIN LAYERS," the disclosures of which are incorporated herein in their entireties.

TECHNICAL FIELD

The present invention relates to a device and method for applying a composition on skin layers such as the epidermis. The invention is particularly interesting for applying compositions on epidermal deformities such as (water) warts, callus formation, corns, fibromas, keratosis pilaris, actinic keratosis or clavi. By extension, the present invention can also be applied for other skin problems of epidermal origin such as birthmarks.

BACKGROUND

In order to treat skin problems, as well as for cosmetic purposes, liquid compositions are often applied on or in the skin. This is often realized topically (for example with an applicator) of via an injection.

Epidermal deformities are an important skin problem. Up until now, two main methods are known for the topical treatment of epidermal deformities such as warts. On the one hand, an acid-based treatment (keratolytics) is known, in which the infected skin or the deformity is dabbed with an acid-based composition such as salicyclic acid, trichloroacetic acid, monochloroacetic acid, formic acid or a mixture of these acids with for example lactic acid. The deformity will as it were weaken and will spontaneously fall off after completion of the treatment. Dead skin cells can be removed before the start of the treatment by means of for example a pumice stone, file, etc. A second, common method is cryotherapy, substantially involving freezing the deformity (in general with liquid nitrogen, but e.g. also a mixture of dimethyl ether/isopropane, . . . ), by which a blister arises between the deformity and the epidermal layer and by which the deformity ends up by coming off. Other used treatments include surgical removal of the deformity, laser or infrared treatment, etc.

Acid-based treatment appears to be a very effective treatment against epidermal deformities such as warts (mostly caused by human papilloma viruses), callus, corns, clavi, . . . .

The treatment method is easy to apply and has a relatively high success rate. In the current cases, the deformities are dabbed with the acid-based composition, for example by means of an applicator or little brush. Such an applicator is amongst other things described in EP 2 407 151 and EP 1 450 771. The disadvantage is however that only the upper layers of the deformities are treated, and that the treatment is moreover not very precise. It is often difficult to target only the infected skin, and often the surrounding, healthy skin is also treated. This leads to unnecessary damage of healthy tissue.

With needleless injection devices, it is possible to apply the liquid composition more precise on or in the skin, without having to perforate the skin by a needle. U.S. Pat. No. 5,026,343 describes such an injection device, in which an internal force-displacing element can be tensioned. When releasing this element, the content of an installed cartridge will be pushed out and applied subcutaneously. For tensioning the spring mechanism, use is made in U.S. Pat. No. 5,026,343 of an electric motor operated by a battery. As a result, the injection device has only a limited life time and is not environment-friendly. The document also describes a user-friendly way of installing cartridges in the injection device, avoiding direct contact with the hands of a user. However, for removing the cartridge after use, a user must pull the injection side of the cartridge. On this side however, rests of the chemical composition often stay behind, that have not been absorbed sufficiently by the skin to treat. As a result, the fingers of a user can unintentionally come in contact with the often acid-comprising liquid composition, which can lead to irritation of the fingers.

U.S. Pat. No. 6,053,890 describes a needleless injection device provided with replaceable cartridges. The cartridges described in this document can be attached to the injection device by means of thread or bumps. After releasing the liquid composition, a user must again take the cartridge close to the injection gap, as a result of which fingers can unintentionally come into contact the liquid composition. The use of this injection device thus again leads to the dangerous situations as described above.

Thus, there is a need for a method for applying a composition such as a liquid therapeutic composition in a controlled and efficient way on the skin such as on and in the epidermal layer or the deformities. Moreover, there is a need for a kit, comprising an injection device and cartridges, that constitutes a user-friendly and more secure alternative and that can prevent irritation of the hands when removing the cartridges after use.

It is the goal of the present invention to provide a device and a method that can in a controlled and professional way apply an amount of a composition on the skin, such as on an epidermal deformity, in such way that only the target area is targeted and no other skin comes in contact with the composition.

It is a further goad of the present invention to provide a leak-proof device, that is easy to use and guarantees absolute safety to the user.

SUMMARY

To this purpose, the invention provides a kit comprising an injection device and one or more cartridges for applying a liquid composition on the skin according to claim 1. The kit is simple and safe to use, prevents leakage and contact between the hand of a user and the liquid composition when removing a cartridge, ensures a precise dosage and is moreover more efficient in operation than the known systems, as the composition can be applied in the deeper skin layers without an injection with a needle. The kit thus guarantees a painless use as it works needleless.

The kit is in particular extremely appropriate for home treatment of epidermal deformities. The deformity will be better treated and will disappear quicker or less treatments will be needed.

In a second aspect, the invention provides a method for applying a liquid composition on the skin, according to claim 18. As a result of the needleless injection of a composition under increased pressure, the method is painless and moreover extremely efficient.

DETAILED DESCRIPTION OF THE FIGURES

FIGS. 1A and 1B show an embodiment of a kit according to the present invention, comprising an injection device and cartridges.

FIGS. 2A to 2C is a step-by-step presentation of the use of a kit according to the present invention for applying a composition onto the skin.

FIG. 3B shows a perspective view and cross-sectional view of such a cartridge.

FIGS. 3C and 3D are also embodiments of possible cartridges according to the present invention.

FIGS. 7A to 7C show a device according to the present invention in rest position.

DETAILED DESCRIPTION OF THE INVENTION

Figure 2B:
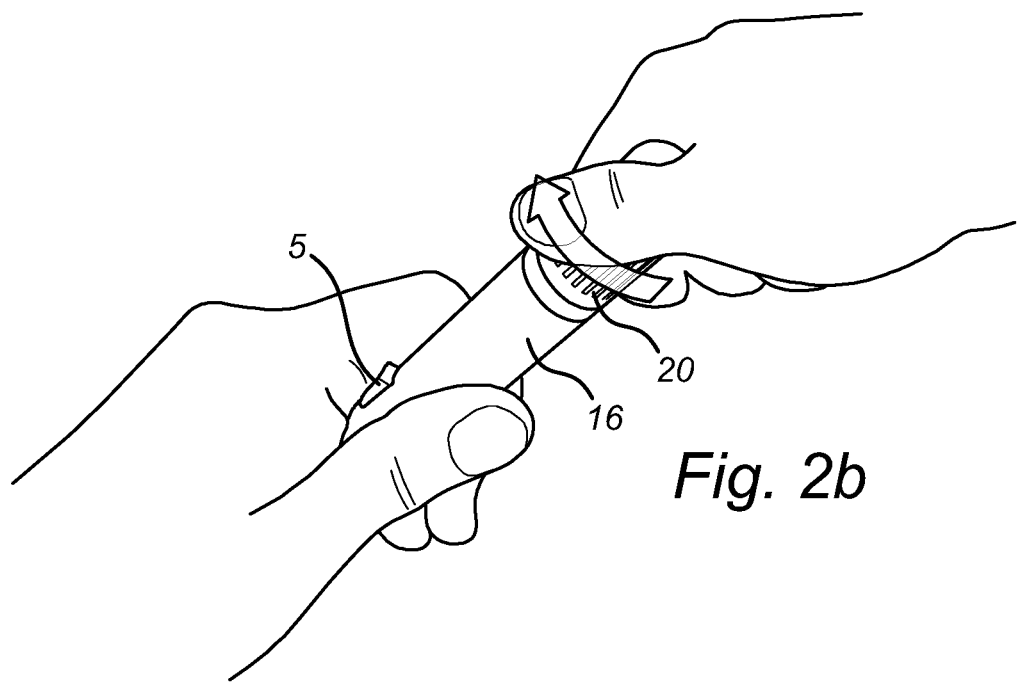

The goal of the present invention is to provide an efficient, quick and painless way for applying a liquid composition on or in the skin. The present invention is particularly appropriate for applying a composition on or in epidermal deformities such as (water-)warts, callus formation, corns, fibromas, keratosis pilaris, actinic keratosis or clavi, etc.

In a first aspect, the invention therefore provides a kit for applying a liquid composition on or in the skin. The kit particularly comprises an injection device and one or more cartridges, in which the cartridges are provided with a container that is appropriate for receiving a liquid composition. The injection device comprises a casing and is distally provided with means for receiving a cartridge.

The kit according to the present invention has the advantage that the composition can be provided separately from the actual injection device. As an immediate consequence, the device can therefore be reused and can be provided with cartridges with different content (different formulations and/or volumes), according to the specific application (e.g. higher volume for deeply rooted warts, small volume for hand warts). This also prevents leakage of the device, particularly if use is made of a composition based on acid or alkaline, of which it is known that they attack the polymers of which such devices are often composed.

Moreover, the cartridge is easy to install in the device and is also only temporary present, namely only during the effective use of the device. After that, the cartridge can easily again be removed and the used cartridge can be disposed of.

According to an embodiment of the present invention, the injection device will internally in the casing be provided with a force-displacing element that can be shifted in the longitudinal direction of the injection device by means of a spring mechanism. By using a spring mechanism, a particular force can be generated, that can subsequently be transferred to the force-displacing element that in turn can transfer the force to push out a liquid that is in the cartridge (when this is attached to the device).

The distal end of the force-displacing element will preferably be movable between a position within the casing and a position at of past the distal end of the device. With this, the highest position in the casing will correspond to the position, in which the force-displacing element is loaded at maximum with a force, and the lowest position will correspond to the position in which the force is transferred to the cartridge or its parts (if present).

In an embodiment according to the present invention, the casing of the injection casing will internally be cylindrical or substantially cylindrical. In a further embodiment, the cylindrical internal casing will be tapered to a truncated cone.

The force-displacing element will be movable by means of any suitable mechanism known in the state of the art. The force-displacing element will preferably be driven by a spring mechanism determining the position of the element in the casing. The force-displacing element will in particular be attached at one side to a spring, such as a compression spring. This will in particular be the side faced to the proximal end of the injection device. By tensioning the spring, the force-displacing element will be raised in the casing of the injection device. By subsequently releasing the spring at a predetermined moment, the force-displacing element will be lowered in the device with a particular force, causing the liquid present in the cartridge to come out of the cartridge in the direction of the skin.

In a preferred embodiment, the casing of the injection device will at the proximal end be provided with a tensioning system for the spring mechanism. This can in particular be a turning mechanism, in which the user can tighten the internal spring mechanism at the outer side of the device. This tensioning is realized by turning an external turning knob at the proximal end of the device and internally connected to the spring mechanism one or several times around a longitudinal axis of the device. When feeling resistance, the spring will be maximally tightened and the user will know the device is ready for use.

Furthermore, the casing can internally be provided with a user-operated release mechanism such as a push button, for releasing the spring mechanism, as a result of which the release of the composition is initiated. The release mechanism is preferably positioned at or past the centre line of the injection device, in the direction of the distal end of the device. This increases the user-friendliness of the device.

In a preferred embodiment, the spring mechanism will be tightened by means of a thread element that is located in the casing and that is provided at the external side with a thread. In specific circumstances, this element will be engaged to a thread of the casing. The thread element has a variable opening of which the diameter can be adjusted. This adjustment is realized by means of a rod-shaped element located in the opening of the thread element. At the thread element(s), the rod-shaped element has a cross-section with a different length and width. In an embodiment of the rod-shaped element, the cross-section is elliptical or oval. In another embodiment, the rod-shaped element is provided with lip-shaped structures. The position of the rod-shaped element in the opening determines the diameter of the opening of the thread element and consequently also the position with respect to the thread in the casing. When the thread element is in a widened position (after correct positioning of the rod-shaped element), the thread element will be engaged to the thread of the casing and will be able to move upwardly (by means of a turning mechanism in the proximal end). By means of the upward movement of the thread element, sufficient force can be applied to a spring of the spring mechanism, present at the proximal end of the casing. The force-displacing element is preferably connected to the spring mechanism and when tensioning the spring mechanism, it will be moved upwardly in the direction of the proximal end of the casing. When releasing the spring mechanism by pushing in a release mechanism, the force-displacing element is moved downwards and a sufficient force will be generated to push a liquid out of a cartridge, if present in the device.

In an embodiment, the rod-shaped element and the force-displacing element are separate, mutually connected parts. In another embodiment, the rod-shaped element and the force-displacing element form one entity.

In another embodiment of the present invention, next to a force-displacing element, a movable body will be provided in the device in the container of the cartridge. The movable body will preferably be mobile in the direction of a longitudinal axis of the cartridge. The movable body will in particular be placed above the liquid in the container. The term "above the liquid" means that the body is positioned above or adjacent to the liquid surface, or that the volume of the body is positioned maximally 5% in the liquid.

The presence of a movable body in the container of the cartridge further causes the liquid present in the container to come out of the cartridge with a predetermined pressure, dependent on the force applied to the movable body. Due to the specific construction of the device and the cartridge, the used composition will at no moment come into the device. This increases the life time of the device. The movable body will preferably be composed of an acid-resistant polymer. In a preferred embodiment, the acid-resistant polymer will be chosen from the group comprising polyphenylene sulfide, polyoxymethylene, polypropylene, polyethylene, preferably ultra-high molecular weight polyethylene (UHMW-PE), co-polymers of acetal, ethylene vinyl acetate (EVA), polyethylene terephthalate, thermoplastic polyester elastomers (TPE-ET), polycyclohexylenedimethylene terephthalates (PCT), polybutylene terephthalates (PBT), halogen-free liquid crystal polymers (LCP), PC-ABS or combinations.

The operation of the device in which the cartridge is provided with an additional movable body in the container of the cartridge is similar to that of the embodiment without movable body. By means of the spring mechanism, the force-displacing element will internally be mobile. When activating the device, the force-displacing element will be brought upwardly in the casing of the device. Subsequently, this will move downwards with a defined force, generated by the spring mechanism, and after pushing in the operation mechanism, by which the force-displacing element will collide with the movable body. The force of the force-displacing element will then be transferred to the mobile element, as a result of which the said mobile element begins to move. As a result of this movement, the underlying liquid composition is pushed out of the cartridge with a predetermined pressure.

The movable body will in particular only be mobile in the direction of a longitudinal axis of the cartridge. To this end, the movable body is closely comprised in the cartridge. To this end, the movable body will have a maximum periphery that is smaller than the maximum periphery of the container, so that movement in the longitudinal direction of the container is made possible, but movements in the lateral direction are limited. The maximum outline of the cartridge is more in particular maximum 10% smaller than the maximum outline of the container, more preferably this is maximum 5%.

The movable body can have on any possible form. The movable body is preferably cylindrical.

The said embodiment has the advantage that the parts of the device will at no time come into contact with the acid, thus increasing the life time of the device.

In both embodiments, the cartridge will have a distal and a proximal end; in which the distal end is located furthest from the device and is faced to the skin surface when the cartridge is installed in the device. The proximal end is preferably located at the receiving means of the cartridge. The liquid is removed out of the cartridge via the distal end of the cartridge.

In a preferred embodiment, both ends are provided with a closing means. The closing means can comprise of a multi-layered or single-layered film, for example from metal or plastic, a paper layer or a composite material. In another embodiment, the closing means will comprise a polymer, such as for example rubber, polypropylene, PC-ABS, etc.

In an embodiment, at least one of these closing means will be removable by the user prior to the application of the composition. In the present context, the term "removable" means that the closing means can be separated in full or in part of the cartridge or that it no longer performs its closing function. 'Removable' can thus refer either to the physical removal or taking off of the closing means, or to the prevention or interruption of the functionality of the closing means.

In an embodiment according to the present invention, at least one of the closing means will be manually removable, for example by means of a pulling, turning or tearing movement or via the rupture of the closing means.

In case of use of a film or a paper layer, the closing means can, to this end, be provided with a releasing agent such as silicon or derivatives, and materials with a low surface energy, allowing the removal of the closing means off the underlying surface of the cartridge.

In another embodiment, at least one of the closing means will be broken or teared, for example under the influence of a force applied to the closing means. In a preferred embodiment, this force will be applied by one of the parts of the injection device and/or the cartridge. This closing means is preferably attached by means of ultrasonic welding or laser techniques. The closing means is flexible and extends in the direction of the injection point when the force-displacing element is moved downwards and comes into contact with the closing means.

In a preferred embodiment, the closing means at both the distal and the proximal end are breakable or elastic or can be teared or broken by means of application of a force.

In another, more preferred embodiment, the closing means at the proximal end of the cartridge can be broken (through), stretched or teared by applying a force by means of one or more parts of the device, while the closing means at the distal end of the cartridge can be removed manually by the user, for example by tearing off or breaking off or turning (e.g. via a thread).

The proximal and the distal end are preferably not symmetric with respect to an axis through the transversal direction of the cartridge. With other words, the proximal end of the cartridge will have a different form than the distal end. The distal end will in particular have inclined side walls comprising an injection tip or injection point. The term 'injection tip' or 'point' refers to a part of the cartridge, in which the side part of the cartridge and/or of the internal container is inclined to a point or sharp surface. The injection point or tip will be provided with an opening to the outer side and is coupled to the container. The injection tip or point will serve to evacuate the composition in the container. The evacuation will preferably be realized under increased pressure while the injection tip is located above or on the targeted place.

The cartridge can be provided with an injection device of the kit. The said injection device comprises a casing, in which the casing is provided at the distal end with a recess appropriate for receiving a cartridge. In a preferred embodiment, the edge of the recess can be provided with a thread, for simplifying the installation of the cartridge and fixing it to the device.

In a preferred embodiment, the cartridge will comprise a peripheral edge, in which the peripheral edge is appropriate for installation in the recess of the injection device. In an embodiment, the cartridge will be able to be pushed via the peripheral edge into the injection device and will temporarily be retained in the injection device. In another embodiment, the cartridge will be installed via a thread mechanism.

The container will preferably be enclosed by the peripheral edge. In a preferred embodiment, the container is provided with a symmetrical peripheral edge, in which as much peripheral edge is present at all sides of the container. In another preferred embodiment, the container is provided with an asymmetric peripheral edge, in which at least one side of the container has a larger peripheral edge than the corresponding opposite side. A similar configuration can preferably offer an advantage when the cartridge is taken by a user and installed in (or removal out of) an injection device. The larger peripheral edge can thus serve as a handle, support or grip for the cartridge. The peripheral edge is preferably located at the proximal end of a cartridge, while the injection tip is located at the distal end of the cartridge. When using the injection device, it is possible that rests of the acid-comprising composition are not absorbed by the skin and thus stay behind around the injection tip. When removing the used cartridge, it is thus possible that these acid-comprising rests come into contact with the skin of the hands, as a result of which damage and irritation can appear. Because the peripheral edge (comprising the handle) is located at the opposite side of the injection tip of the cartridge, no rests of the chemical composition can stay behind on the handle and thus, the skin not intended to be treated, does not come into contact with the composition. A similar cartridge thus forms a safe alternative for the cartridges known in the state of the art.

In a preferred embodiment, the peripheral edge provided at the proximal end of the cartridge can be pushed into the recess provided at the distal end of the injection device. This offers a user-friendly way for installing and removing a cartridge in the injection device.

In a possible embodiment, the distal end of the injection device comprises a second spring system that can help a user to place the injection device onto the skin as desired. The second spring system preferably comprises a safety mechanism, preventing the force-displacing element to move along the longitudinal axis of the device when the second spring system is not pushed in, even if a user pushes in the releasing mechanism. Thanks to this additional safety feature, it can be avoided that the composition is released accidentally, thus avoiding dangerous situations. In an alternative embodiment, the force-displacing element can be released if the spring in the tip of the injection device is not pushed in, but the chemical composition will not be delivered, because the force-displacing element does not come into contact with the closing means of the cartridge. The tip of the injection device can preferably only be pushed in if the injection device is tightened/loaded. In this way, the force-displacing element can be avoided to push the composition already out when the injection device is placed on the skin and the force-displacing element is still in the downward (released) position.

The preferred embodiment of a cartridge of a kit according to the present invention is as follows: a cartridge comprising a container with a predetermined amount of liquid composition such as an acid composition, in which the container is internally provided with a movable body that is closely comprised in the container and located above the liquid surface. The container is provided with a peripheral edge at the upper side, the proximal part of the cartridge. Both the proximal and the distal part of the cartridge have an opening, in which the opening will be closed by a removable closing means. The opening at the distal part will in particular be provided in an injection tip or point and will have a smaller diameter than the opening at the proximal end. This tip or point forms an outlet for the liquid. The opening will in particular have a diameter between 0.05 and 3 mm, more in particular between 0.05 and 1 mm, more in particular between 0.1 and 0.5 mm, more in particular between 0.1 and 0.25 mm, such as for example 0.2 mm. As a result, the composition can be applied locally and precisely onto the skin. The chosen diameter further ensures that a sufficiently high pressure can be generated during the evacuation of the solution out of the cartridge, as a result of which the latter can penetrate deeper in the skin layers.

In a preferred embodiment, the kit will comprise several cartridges, in which the exact number depends on the specific application. The kit can for example comprise sufficient cartridges for 1 treatment. The cartridges can all be provided separately or in a package such as a strip, in which the cartridges are mutually attached and can be released individually.

The composition will in particular be evacuated out of the device with a high pressure and will be applied to or injected in the skin with a high pressure, such as at or in an epidermal deformity. In the context of the present invention, the term 'epidermal deformity' refers to any visible (abnormal) deformity, thickening and/or change at the epidermis, resulting from for example, but not limited to, friction, pressure, viral infection, bacterial infection, fungal infection, accumulation of pigment cells. The epidermal deformity will in particular be a deformity of the type (water-)warts, callus formation, corns, fibromas, keratosis pilaris, actinic keratosis or clavi.

The known applicators used in the context of epidermal deformities are only effective on the upper layers of the deformity. Deeper skin layers are not always treated as it will be difficult for the liquid to penetrate to this depth. The disadvantage thereof is that the treatment will last long, especially for bigger deformities. In the present method, the composition will as it were be "bombed" in the deformity, in which not only the upper epidermal layers of the deformity are targeted, but also the underlying layers, that cannot be reached via conventional applicators. All layers of the epidermis will preferably be able to be treated by means of the present invention (stratum corneum, stratum lucidum, stratum granulosum, stratum spinosum). In a preferred embodiment, the composition will be applied to a depth of 0.5 cm (measured from the outer epidermal layers) in the deformity, more in particular to a depth of 0.3 cm, more preferably to a depth of 0.05 mm to 0.5 cm. Moreover, the application is painless, and easy to perform at home.

The term 'at least partially in the deformity' means that at least 20% of the liquid applied by means of the present method will be applied in the deformity under the first surface layer of epidermis cells. In a further embodiment, at least 25%, more preferably at least 40 to 50%, most preferably 70% of the applied composition will be applied under the first surface layer of epidermis cells of the deformity.

The force used will hereby depend on the specific application and the nature and the location of the deformity. The force used will preferably be higher than 50 N, more preferably, it will be between 50 and 250 N, more preferably between 50 and 200 N, still more preferably between 60 and 160 N. In an embodiment; the force can be adapted, depending on the application, the nature and the location of the deformity. Tests have shown that a force between 60 and 110 N is extremely appropriate for little warts, while 160 N is appropriate for plantar warts, overgrown with a thick layer of callus. The force is generated by a combination of force replacement of the internal parts of the device and the evacuation of the composition through a small injection point or tip.

The composition is preferably injected in a volume between 0.5 and 250 µl, more preferably between 0.5 and 50 µl, more preferably between 5 and 25 µl, still more preferably between 5 and 20 µl, still more preferably between 5 and 10 µl such as 6 or 8 µl. Each cartridge will preferably comprise one single dose of the composition. The inventors have found that this volume range was extremely appropriate for treatment of deformities, and simultaneously ensured an optimal absorption through the skin. Amounts out of these ranges were either suboptimally effective or not effective at all, or could not be absorbed by the skin, with loss of the composition as a result.

Although the kit according to the present invention is preferably used in the context of epidermal deformities, the application possibilities are much broader. Basically, it can be used for any composition that can be applied on or in the skin, such as therapeutic compositions, but also non-therapeutic compositions such as inks or cosmetic products. In an embodiment, the kit will comprise cartridges with different compositions so that several applications are possible.

The composition will preferably be an acid-based composition, in which the composition preferably comprises a therapeutically effective amount of acid, selected from the group of fruit acids (AHAs) such as lactic acid, malic acid, wine acid, citric acid and glycolic acid; trichloroacetic acid; monochloroacetic acid; dichloroacetic acid; formic acid; hydrochloric acid, kojic acid, azelaic acid, phosphoric acid, mercaptoacetic acid, retinoic acid, its salts and/or esters, phenols or mixtures of one of the aforementioned substances.

In a preferred embodiment, the composition will comprise at least 1% trichloroacetic acid (TCA), more preferably at least 10% w/w TCA, still more preferably at least 20% w/w TCA, still more preferably in a range between 20 and 50% w/w TCA.

The term 'therapeutically effective' means an amount of ingredients that can realize the targeted effect.

In a further embodiment, the composition comprises a crosslinking/fixing or preserving agent, preferably selected from the group comprising formaldehyde; paraformaldehyde; glutaraldehyde; glyoxal; carbodi-imide; a formaldehyde donor; sodium hydroxymethyl glycinate; diazolidinyl urea; imidazolidinyl urea; dimethylol-5,5-dimethylhydantoin; dimethylol urea; 2-bromo-2-nitropropane 1,3-diol; quaternium-15; parabens; 5-chloro-2 methylisothiazolin-3-on; 1,2-dibromo-2,4-dicyanobutane; ethanol or other alcohols; polyol.

In another or further embodiment, the composition comprises a thickening agent, preferably chosen from de group comprising polysaccharides such as amylose, amylopectin, carbopol, cellulose, carboxymethyl cellulose or its salts, ethyl cellulose, hydroxypropyl cellulose or methyl cellulose, agar agar, acacia gum, glycerin.

Carbopol comprises the commercially available products Carbopol 71 G NF,Carbopol 971 P NF, Carbopol 974P NF, Carbopol 934P NF, Carbopol 980P NF, Carbopol 981P NF, Carbopol 5984EP, Carbopol ETD 2020 NF, Carbopol 934 NF, Carbopol 934P NF, Carbopol 940 NF, Carbopol 941 NF, Carbopol 1342 NF, Pemulen TR-1 NF, Pemulen TR2-NF, Noveon AA-USP and Carbopol Ultrez 10 NF.

The composition comprises preferably at least 0.5% w/w carbopol, more preferably in the range of 0.5 to 3% w/w, still more preferably between 1.5 and 2.5% w/w. It has been found that these ranges offered a sufficient 'rigidity' to the composition and at the same time nevertheless kept it sufficiently fluid for a good penetration in the skin.

Moreover, the composition according to the present invention can also comprise other ingredients such as, but not limited to, plant extracts or plant components (for example derivatives of *Chelidonium majus, Podophyllum peltatum, Betula* sp.), essential oils, etc.

The composition is preferably a water-based composition. The pH of the composition is preferably between 0.5 and 5, more preferably between 1 and 4 while its viscosity is between 20 and 10000 mPa·s, more preferably between 50-10000 mPa·s, more preferably between 100 and 5000 mPa·s, more preferably between 1.0 and 2000 mPa·s at 25° C. (measured according to the 'rotary viscometer protocol' from the European Pharmacopeia Ph. Eur (01/2005:20210) Ph. Eur. 5th edition vol 1, p. 29, chapter 2.2.10. Rotating Viscometer Method). This is important as in case of the use of liquids that are too fluid, leakage of the device according to the present invention can exist. Moreover, a composition with a too high viscosity will cause an obstruction of the device.

Example 1 gives some formulations that are effective in the present invention.

The injection device and/or the cartridge will at least partially be fabricated of an acid-resistant polymer. In a preferred embodiment, the acid-resistant polymer will be chosen of the group comprising polyphenylene sulfide, polyoxymethylene, polypropylene, polyethylene, preferably ultra-high molecular weight polyethylene (UHMW-PE), copolymers of acetal, ethylene vinyl acetate (EVA), polyethylene terephthalate, thermoplastic polyester elastomers (TPE-ET), polycyclohexylenedimethylene terephthalates (PCT), polybutylene terephthalates (PBT), halogen-free liquid crystal polymers (LCP), PC-ABS or combinations.

As use can be made of acids or an acid-base composition, it is important that the device is 100% leak-proof and thus safe. Although the structure of the device and the cartridges (and its operation) in principle prevent that the composition comes into the device, the inventor of the present invention have nevertheless sought polymers that were not affected by acids, as a result of which there is no risk of leakage or damage to the device.

The device and/or cartridges are preferably made by injection moulding or co-injection moulding.

The kit according to the present invention is extremely effective, goal-oriented, easy to use (for example at home) and safe. Moreover, the risk of leakage is reduced to a minimum.

The kit can be offered as one single package comprising an injection device and several cartridges. In a preferred embodiment, the cartridges can also be offered separately, for example if a longer use is needed, or if the use of another composition is intended.

In a second aspect, the present invention also relates to an assembly comprising a device as described above provided with a cartridge according to the present invention.

In a third aspect, the invention provides a method for applying a liquid composition onto the skin. The said method will in particular comprise the following steps:
- providing a cartridge, provided with a liquid composition, in a recess of an injection device;
- positioning the injection device on or at the skin;
- tensioning a spring mechanism; and
- releasing an amount of the composition onto the skin. The composition will in particular be applied under pressure and by means of a needleless injection step. In the context of the present invention, the term 'needleless injection' of 'needlelessly injecting' shall be interpreted as the administration of a liquid or formulation via the skin to a predetermined location and/or depth of a tissue or in the blood stream, in which the skin is not punctures by a needle or sharp object. Hereby use will be made of an increased pressure.

The inventors of the present invention have found that it is important for many applications to apply a composition to a determined depth of the skin layer, instead of superficially onto the upper skin layers. Moreover it appears that a large number of users are afraid of or have a phobia about needles. By offering a needless technique, an optimized method is offered compared to the state of the art.

The force generated during the needless injection will preferably be higher than 50 N, it will be more preferably between 50 and 250 N, more preferably between 50 and 200 N, still more preferably between 60 and 160 N. This force appeared to be optimal to bring the composition in the deeper epidermal skin layers. The composition will preferably be applied in a volume between 0.5 and 250 µl, more preferably between 0.5 and 50 µl, more preferably between 5 and 25 µl, still more preferably between 5 and 20 µl, still more preferably between 5 and 10 µl such as 6 or 8 µl.

The method is particularly appropriate for applying a composition onto an epidermal deformity such as a (water-) wart, callus formation, corn, fibroma, keratosis pilaris, actinic keratosis or clavus.

The present invention thus also relates to a method for the treatment of epidermal deformities.

Preferably a kit comprising an injection device and one or more cartridges according to the present invention is used for applying a liquid composition onto the skin.

EXAMPLES

The invention will now be further described by means of example figures, without being limited thereto.

FIGS. 1A and 1B show an embodiment of a kit according to the present invention, comprising an injection device 2 and cartridges 1. Figure A show a front and side view of the device 2 and an upper and side view of one single cartridge 1 and an supper view of a strip or blister of cartridges 19.

The injection device 1 comprises a casing 16 that preferably takes the form of a pen. A similar configuration is very handy. The casing 16 can be provided with a grip 17 in the form of a small constriction or narrowing in the casing 16. This increases the grip of the user on the device 1. The device has a proximal 3 and distal end 4, in which the distal end 4 will be provided with means 7 for receiving a cartridge 1. The distal end 4 is the end that will eventually face the skin when applying the composition onto the skin. The proximal end 3 will at the outer side be provided with a turning knob 20 that is part of a tensioning mechanism 6. This turning knob is part of the casing 16 and is located at the most proximal end 3 of the device. The turning knob 20 is preferably clearly distinguishable from the rest of the device for the user. The distinguishability is preferably visual, by means of another colour use and/or demarcation. In a preferred embodiment, the turning knob 20 will be provided with grip-increasing elements, such as ribs, grooves or other details. Still preferably, another visual element (e.g. a green or red spot) indicates if the injection device is loaded/unloaded. A cartridge can be provided in the recess before or after tensioning the spring mechanism.

The cartridge 1 can be provided separately or in a multitude of cartridges such as in a strip 19, in which the cartridges are mutually attached and can be released for example by means of a provided perforation or weakening in the strip 19.

Figure 3A:
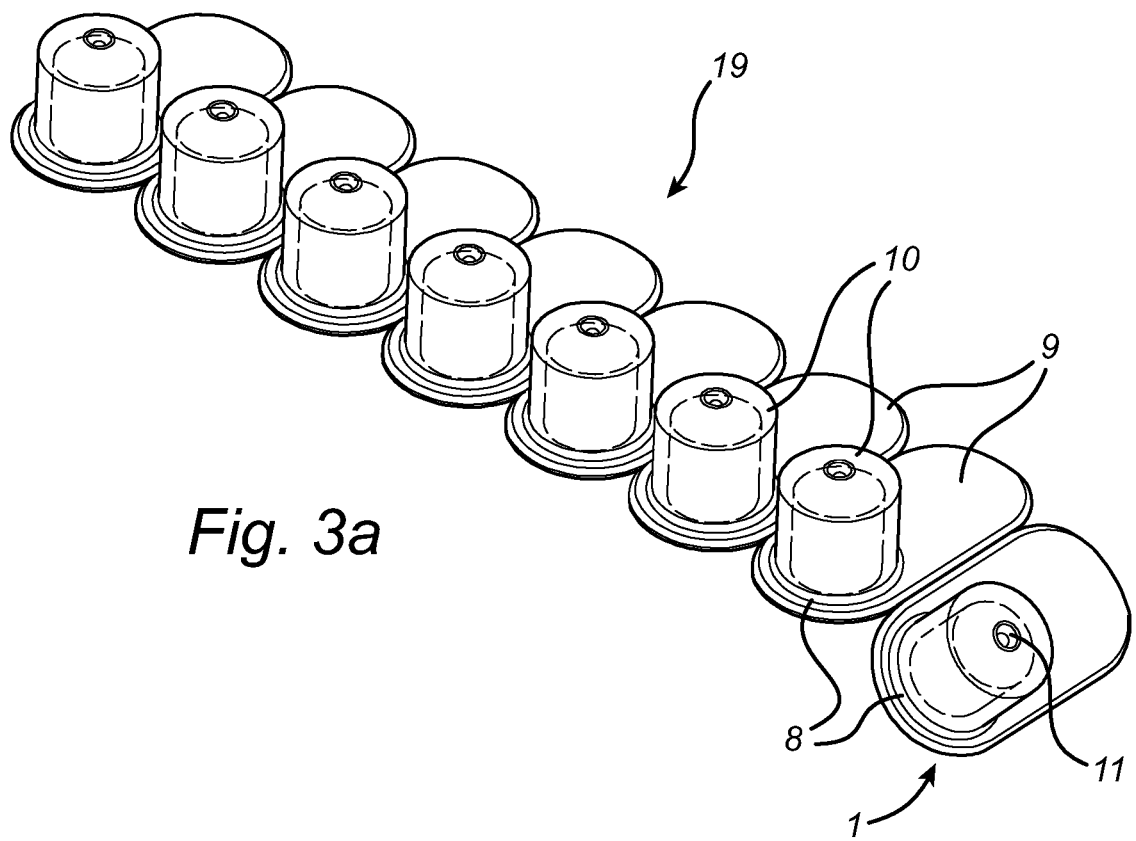
FIGS. 3A and 3B are detailed views of a possible embodiment of the cartridges according to the present invention, in which FIG. 3A gives an overview of a multitude of cartridges in strip
Figure 3B:
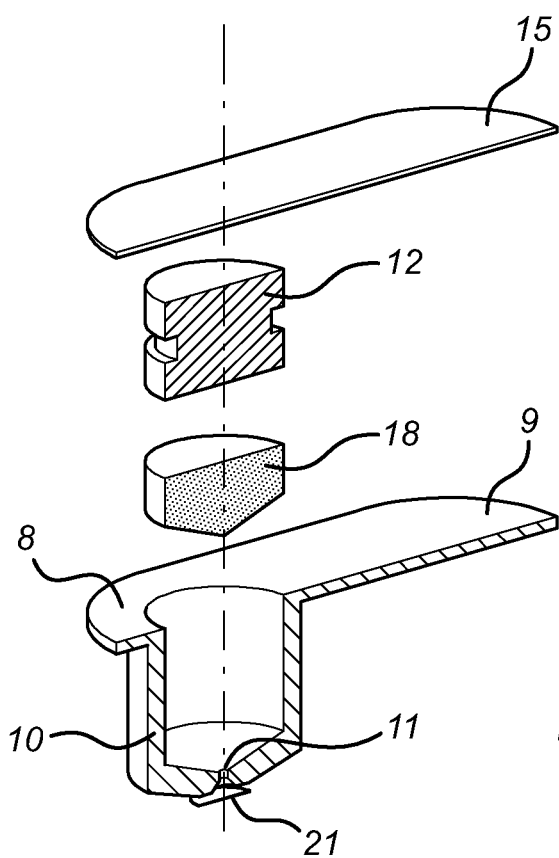
Figure 3C:
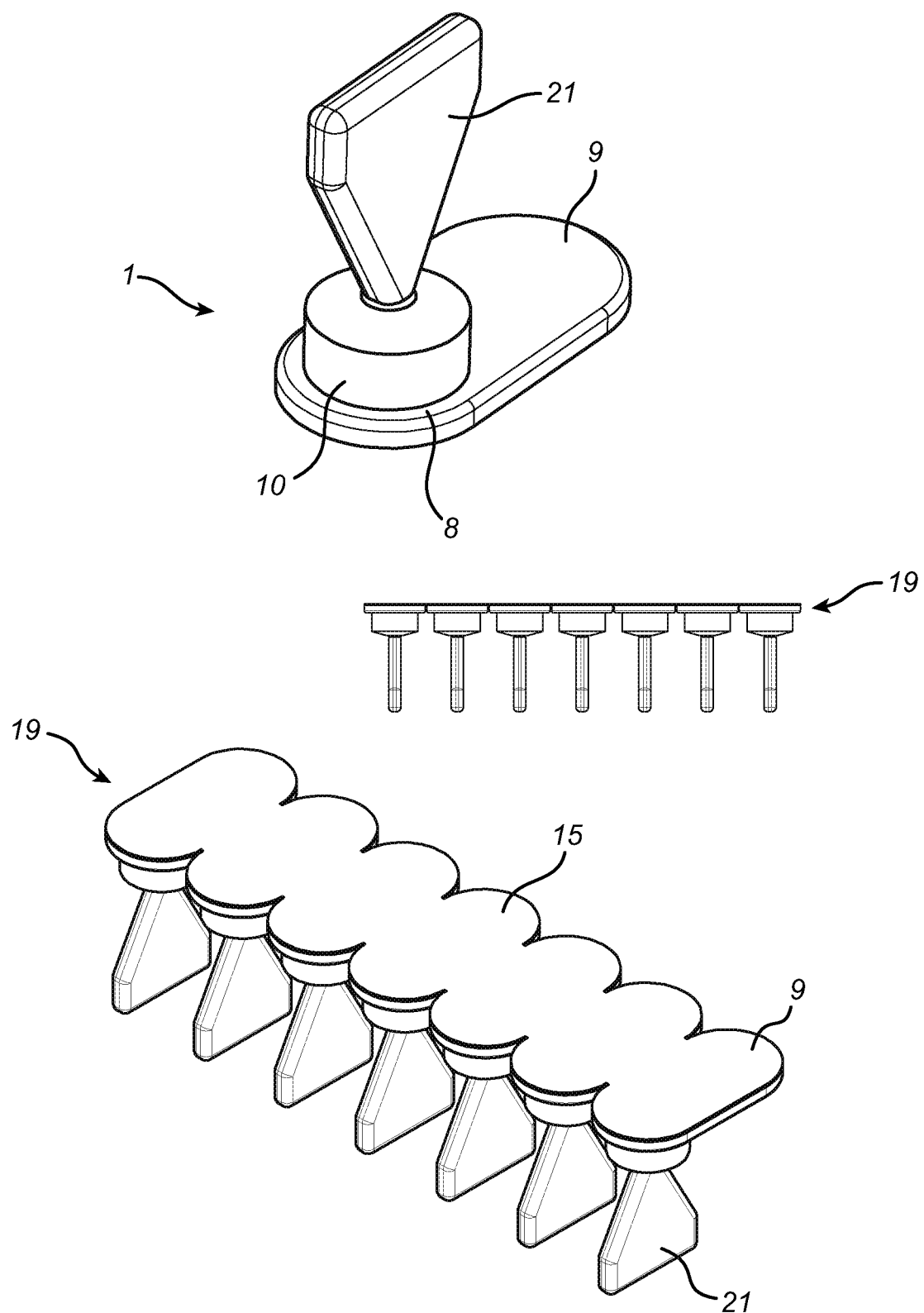

FIGS. 3A and 3B show detailed views of a possible embodiment of the cartridges 1 according to the present invention, in which FIG. 3A gives an overview of a multitude of cartridges in strip 19 and FIG. 3B shows a perspective view and cross-sectional view of such a cartridge 1.

The cartridge 1 preferably comprises a container 10 that is extended in the distal direction of the cartridge. This container is appropriate for receiving a solution that has to be applied onto the skin. The container 10 is located in a plane, sunk with respect to an upper side of the cartridge. The upper side forms a peripheral edge 8 for the cartridge 1 that will extend past the container 1. In an embodiment (not illustrated), the container can be located point symmetrically in the upper side. This is, the container is located in the middle of the upper side, in which the container 1 is equally confined by the peripheral edge 8. In another, more preferred embodiment, such as illustrated in FIG. 3B, the container is located asymmetrically in the upper side, in which at least one side of the container will have a larger peripheral edge than the corresponding opposite side. The longer side of the peripheral edge can thus serve as a handle 9 for the cartridge 1, so that a user can easily take, and install or remove, the cartridge 1.

The upper side, that is basically formed by the peripheral edge 8, and the container (or the container opening) enclosed in the peripheral edge 8 are provided with a closing means 15. This can be a film or paper layer. In another embodiment, this can also be rubber or a polymer. This is preferably an acid-resistant material. The closing means 15 can completely close off the peripheral edge and the container. In an alternative embodiment, only a part of the peripheral edge can be closed off. The container will however at any time be closed off by the closing means 15. In an embodiment, the closing means are not permanently attached to the cartridge, but they can be removed. The removal can be manual by the user, or during the application process of the composition for example by breaking the closing means after applying a force on the closing means 15. If the closing means 15 can be removed manually, the closing means—if it comprises a film or a paper layer—can preferably be provided with a releasing agent at the side adjacent to the peripheral edge 8 and the container 10. This releasing agent can be applied all over the closing means or on a discrete zone of the closing means, for example at a line at the peripheral edge. Due to the presence of the releasing agent, a zone is created that can be easily released from the cartridge by a user.

The closing means 15 ensures that the solution in the container 10 of the cartridge doesn't leak.

A skilled worker will acknowledge that the container 10 can take several forms, and that the form is not limitative. The container 10 is preferably a basically cylindrical compartment that will terminate in the distal direction of the cartridge till an injection point 11. Therefore, the side walls of the container 10 will incline in the distal direction to an opening, an injection point. The diameter of this point is in particular between 0.05 and 3 mm, more in particular between 0.05 and 1 mm, more in particular between 0.1 and 0.5 mm, more in particular between 0.1 and 0.25 mm, such as for example 0.2 mm.

The injection point, that provides the connection between container and outer world, will in particular also be closed off by closing means 21. These closing means 21 prevent leakage of the solution out of the cartridge. The closing means are removable, that is they will not close off the opening permanently. The closing means 21 will in particular be broken off when applying the composition onto the skin, under the influence of the high pressure that is generated and its force. In another embodiment, the closing means 21 are manually removed by the user.

On top of the composition in the container, a movable body 12 will rest that is closely confined in the container 10. The maximum periphery of the movable body will hereby be a little bit smaller than the maximal periphery of the container 10, allowing a movement in the longitudinal direction of the container 10, and limiting movements in the lateral direction. The movable body has a basically cylindrical form. In an embodiment (see FIG. 3B), the movable body 12 can comprise a constriction. This constriction guarantees a friction-lowering effect so that the movable body 12 can easily be moved in the container 10. In FIG. 3d, an embodiment of a cartridge without a movable body is shown.

The amount of the composition in the container will depend on the application. Preferably, one single dose will be present in the container. The composition will in particular be present in a volume between 0.5 and 250 µl, more preferably between 5 and 150 µl, still more preferably between 5 and 50 µl.

Figure 2C:
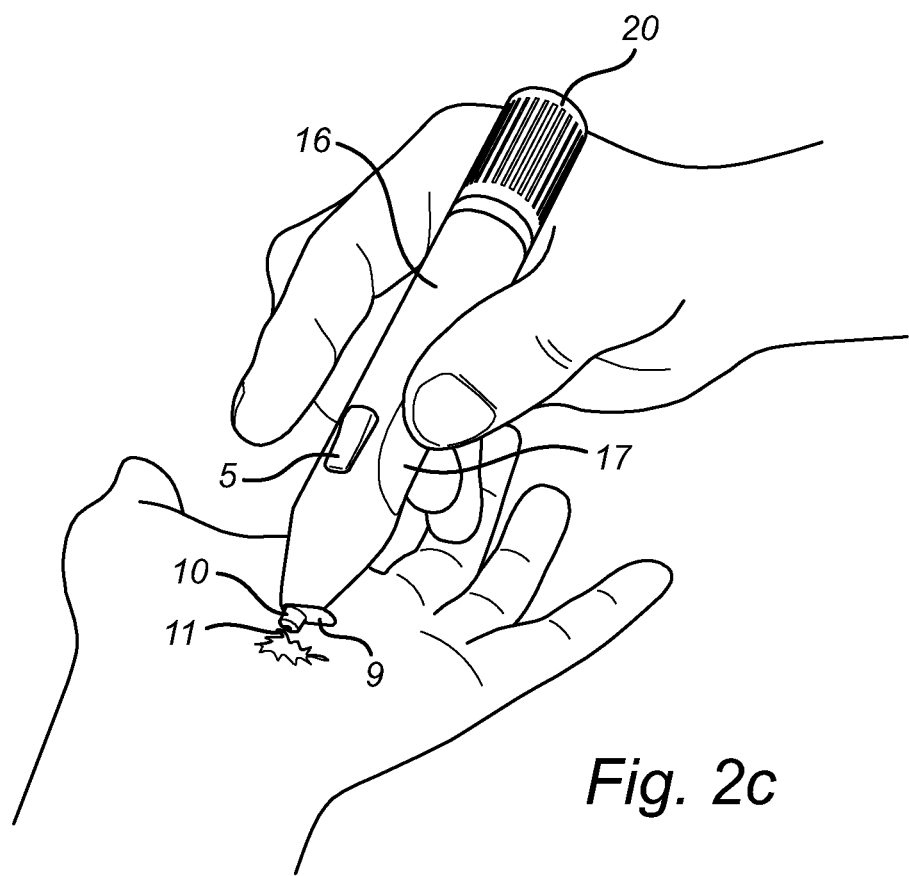

FIGS. 2A to 2C give a step-by-step presentation of a possible use of a kit according to the present invention for applying a composition onto the skin.

In a first step, the injection device 2 will be provided with a cartridge 1 at the distal end of the device (FIG. 2A). Herewith, at least one or both closing means 15, 21 can be manually removed by the user. In a preferred embodiment, only closing means 21 will be manually removed, while closing means 15 will be broken through by application/injection. Subsequently, the user will wind up the internal spring mechanism via the external turning knob at the proximal end of the device 2. The winding-up is realized by tensioning the turning knob 20 (several times) till a light resistance is felt (FIG. 2B). The user then knows that the device is ready to use.

In a last step, the injection point 11 is positioned above or on the location where the composition has to be applied. Subsequently, the user will operate the release mechanism by pushing in the knob on the casing of the device 2. The composition will as it were be fired in the upper skin layers.

Figure 4A:
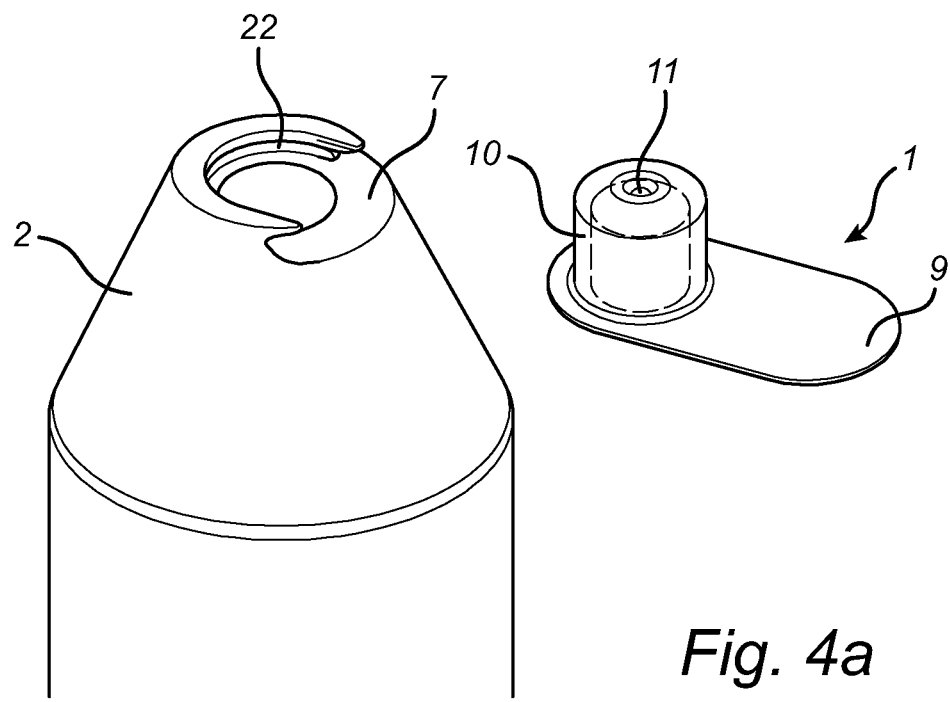
FIGS. 4A to 4B are detailed views for installing a cartridge on the distal end of an injection device according to an embodiment of the present invention.
Figure 4B:
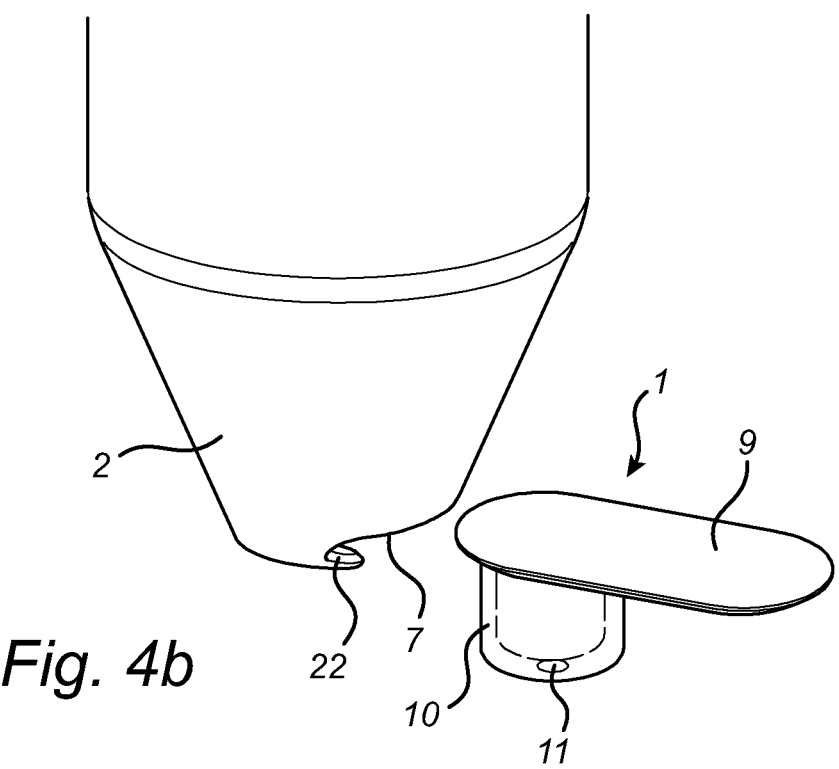

FIGS. 4A and 4B are a detailed view of a cartridge 1 and distal end 4 of an injection device 2, in which a cartridge 1 is installed in an injection device 2. The distal end 4 is provided with a recess 7 appropriate as a receiving means for the cartridge 1. The recess 7 is combined with a lip structure 22 that ensure together that the cartridge fits into the recess and stays there. The installation of the cartridge in the device is realized by a sliding movement. The lip structure 22 ensures that the cartridge stays in place so that it can partially encompass the peripheral edge 8 of the cartridge. The lip structure 22 will in particular have a form corresponding the peripheral edge 8 of the cartridge 1.

In another preferred embodiment, the edge of the device possesses at the recess a thread that allows the cartridge to be positioned and fixed to the device by means of this thread.

In the embodiment shown at FIG. 4B, a part of the peripheral edge 8 and more specifically the handle 9 will protrude from the plane of the device 2. The handle 9 can serve as a mini lever for removing the cartridge out of the device. Before providing the cartridge in the device, the closing means 15 can be removed manually from the proximal end of the cartridge.

FIG. 5 is cross-view of an injection device provided with a cartridge according to a particular embodiment of the present invention and schematically shows the internal operation of the assembly when applying a composition.

Figure 5A:
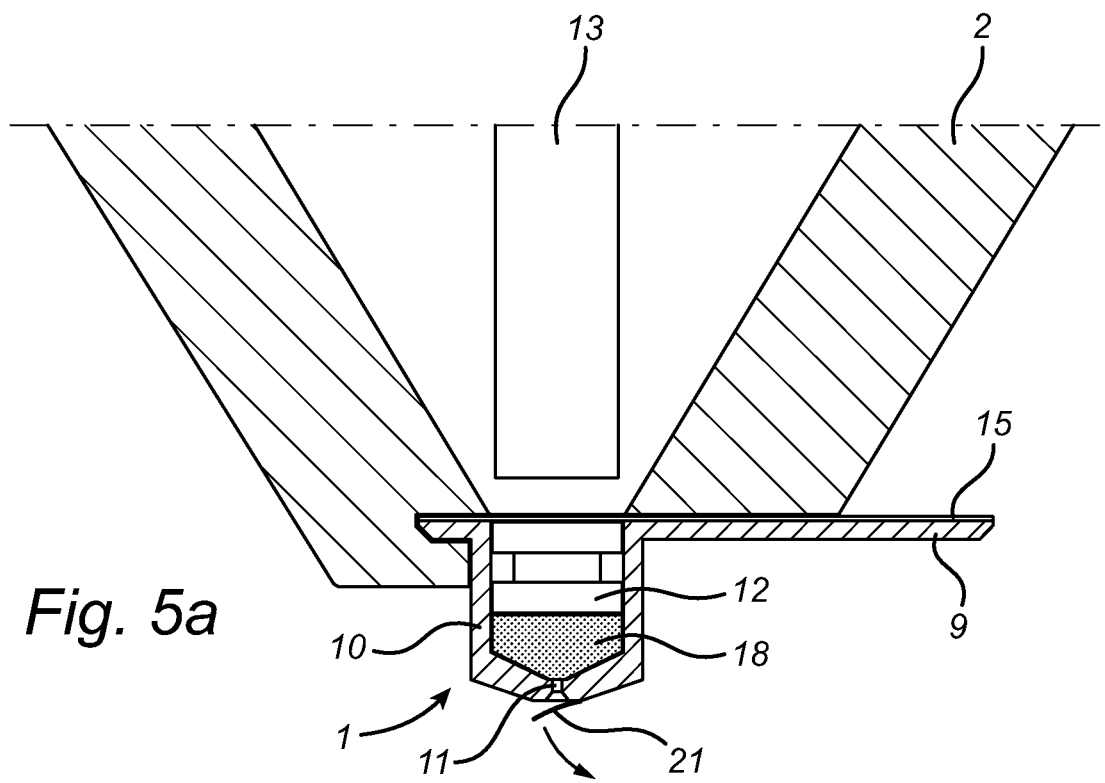
FIGS. 5A to 5F show a cross-sectional view of an injection device provided with a cartridge according to the present invention and schematically shows the internal operation of the assembly when applying a composition.

The cartridge 1 is provided at the device 2 as illustrated in FIG. 4. The cartridge is now incorporated in a removable way at the distal end of the device 2. The cross-section in FIG. 5A shows that the movable body 12 is located above the composition. A force-displacing element 13 such as a piston is located internally in the casing and is connected to a compression spring. The system is still in rest. The closing means 21 can be removed at the distal end of the cartridge.

Figure 5B:
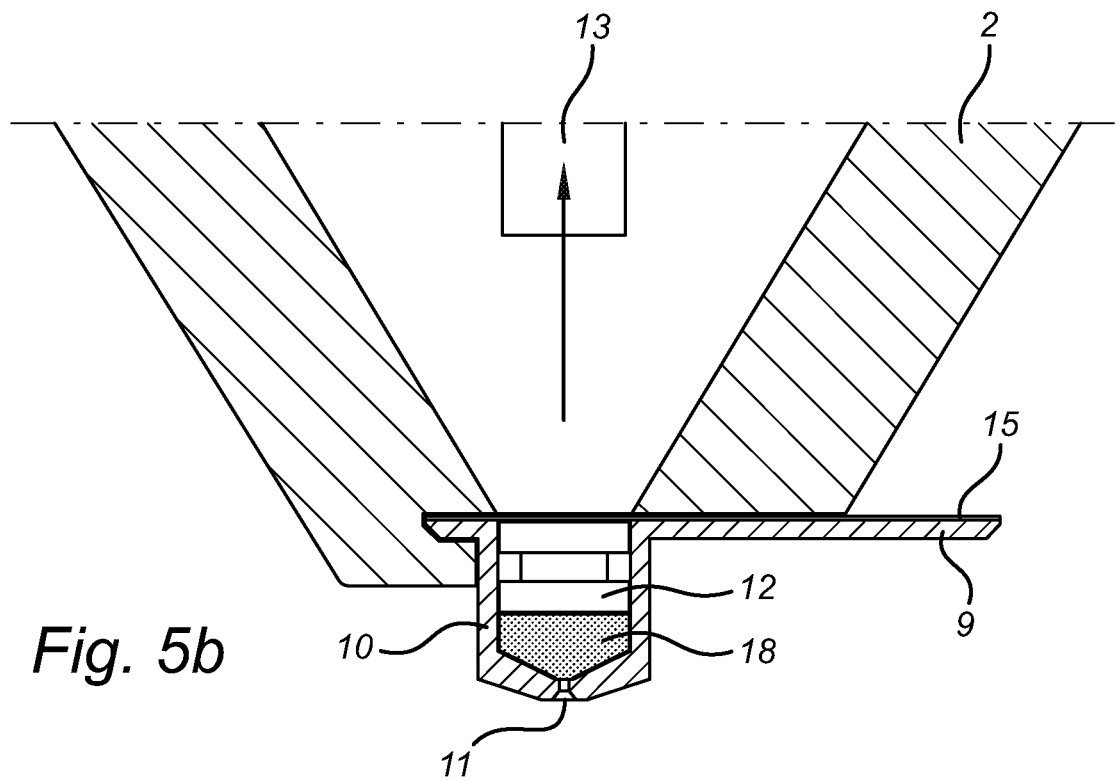
Figure 5C:
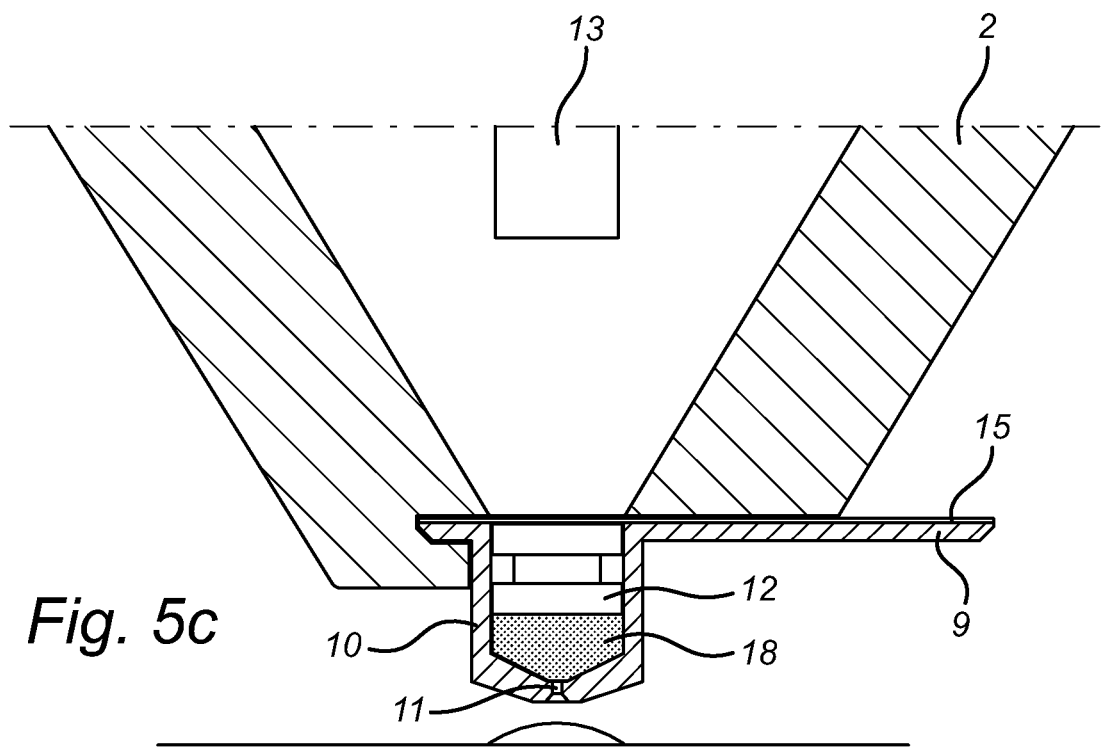
Figure 5D:
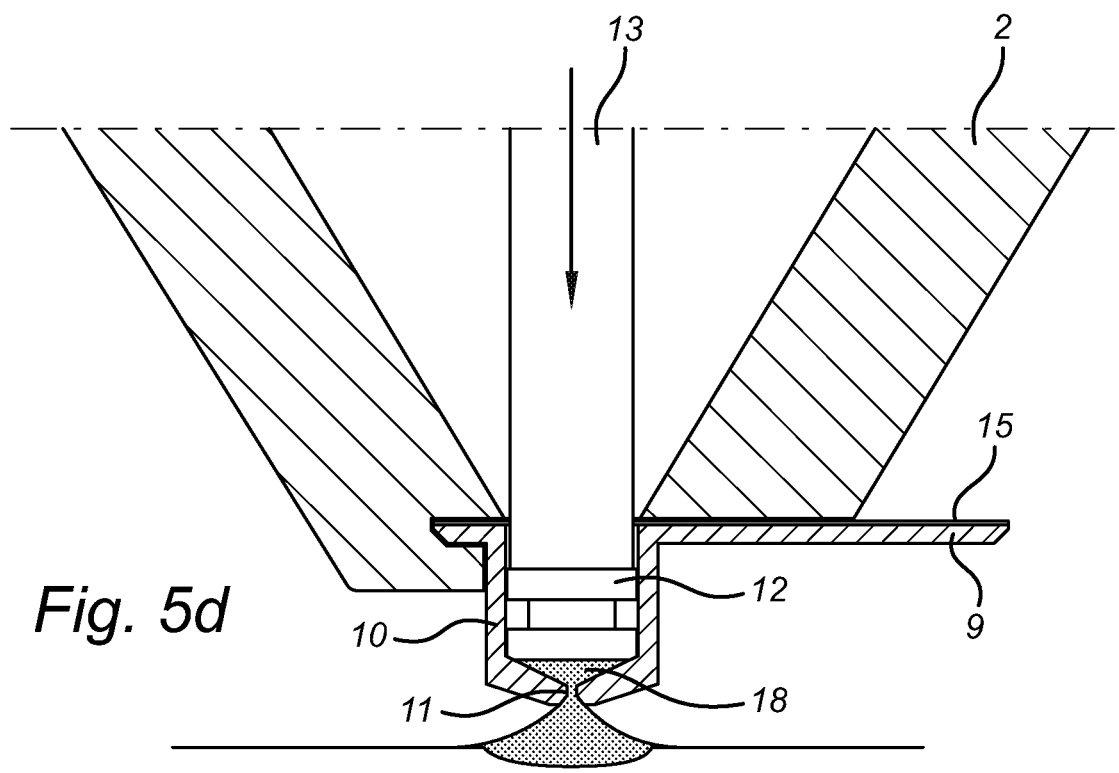
Figure 5E:
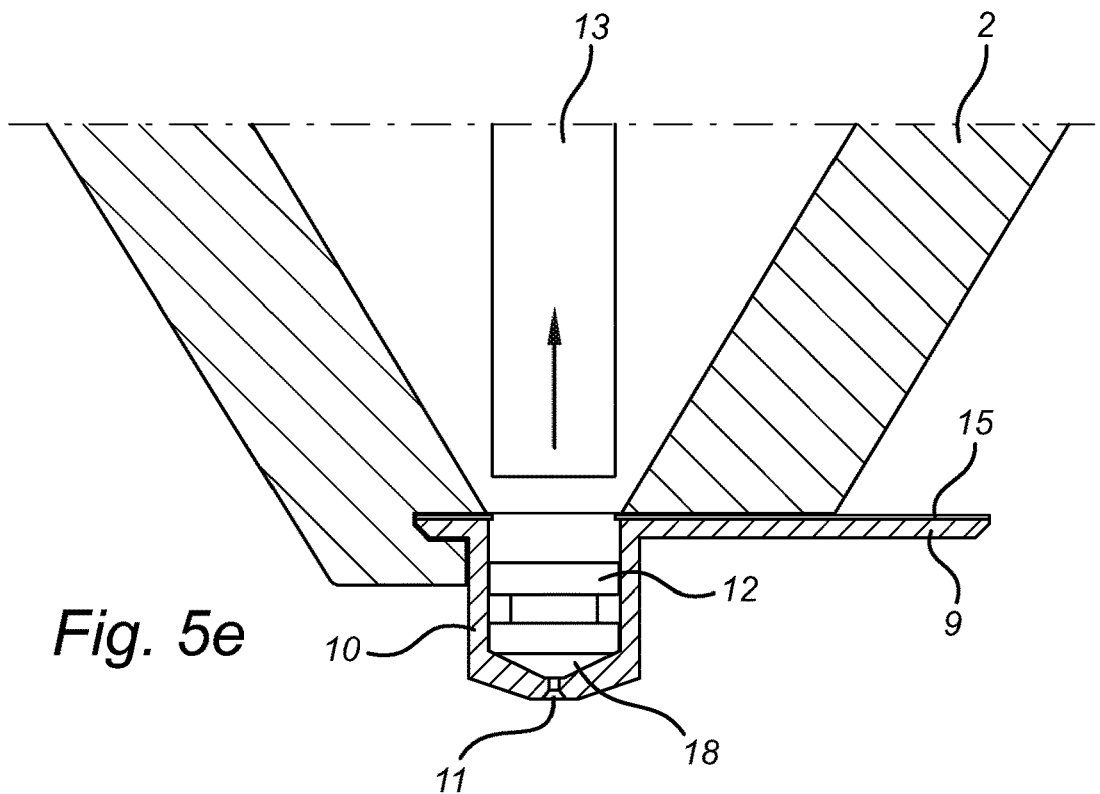
Figure 5F:
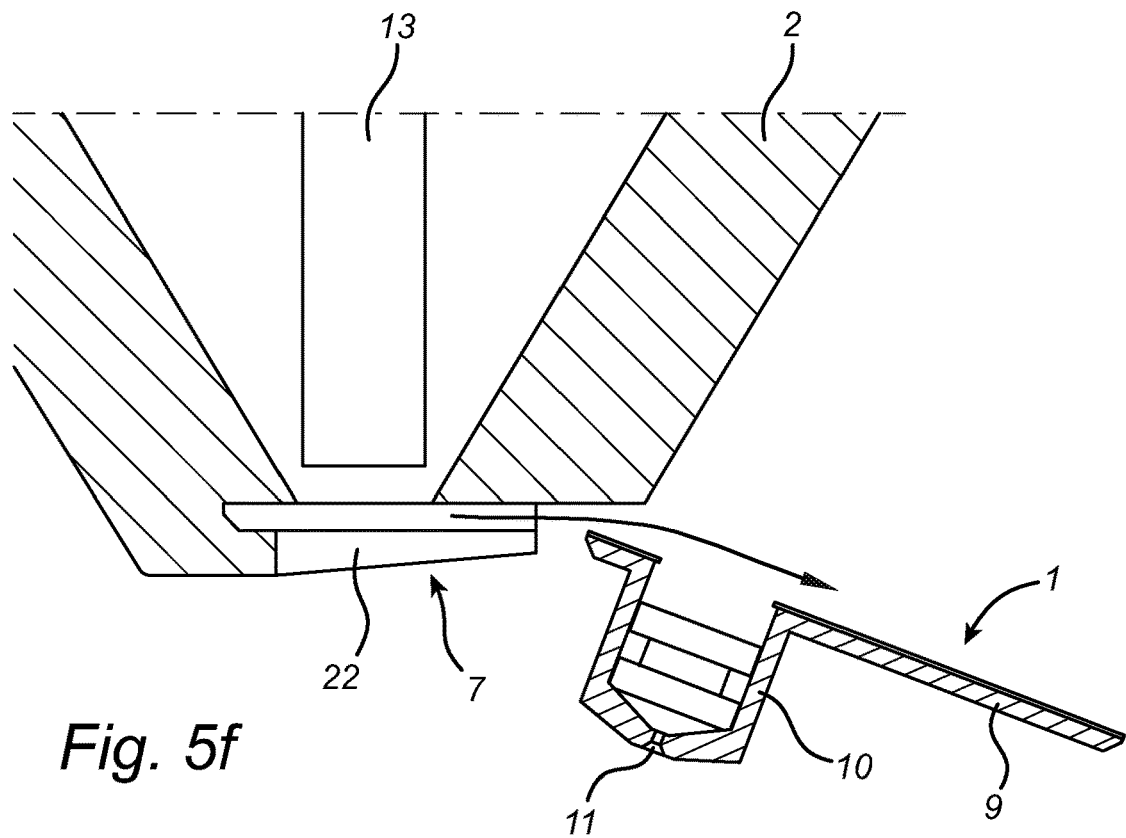

Subsequently, as illustrated in FIG. 5B, the spring will be tightened by means of a tensioning mechanism. As a result, the force-displacing element 13 is raised, in the direction of the proximal end of the device and a force is generated. Subsequently, the injection device can be positioned at a position on the skin. Finally, the spring will again be released by activating the releasing mechanism by the user. Hereby, the piston element will move downwards at a particular force and collide with the movable body 12 in the container 10. By transferring the forces, the movable body 12 will also start to move and move downwards in the container 10. Hereby, the composition, located under the movable body, is as it were pushed out through the injection point 11 at an increased pressure. The composition is introduced in the skin layer at a high pressure and in a needless way (FIGS. 5D and 5E). The empty cartridge can subsequently be removed and the injection device is again ready for use (FIG. 5F).

Figure 6:
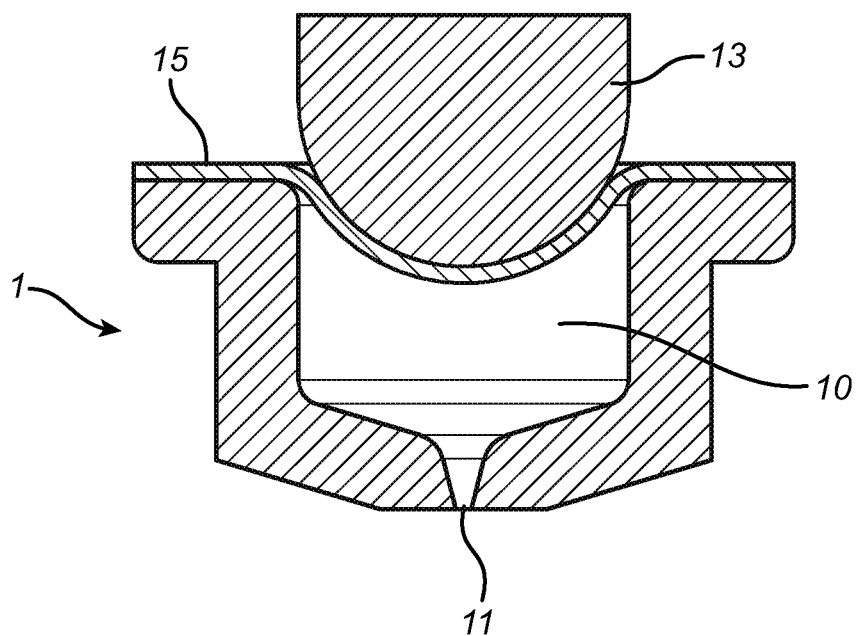
FIG. 6 is a possible embodiment of a cartridge with elastic closing member according to an embodiment of the present invention.
Figure 8A:
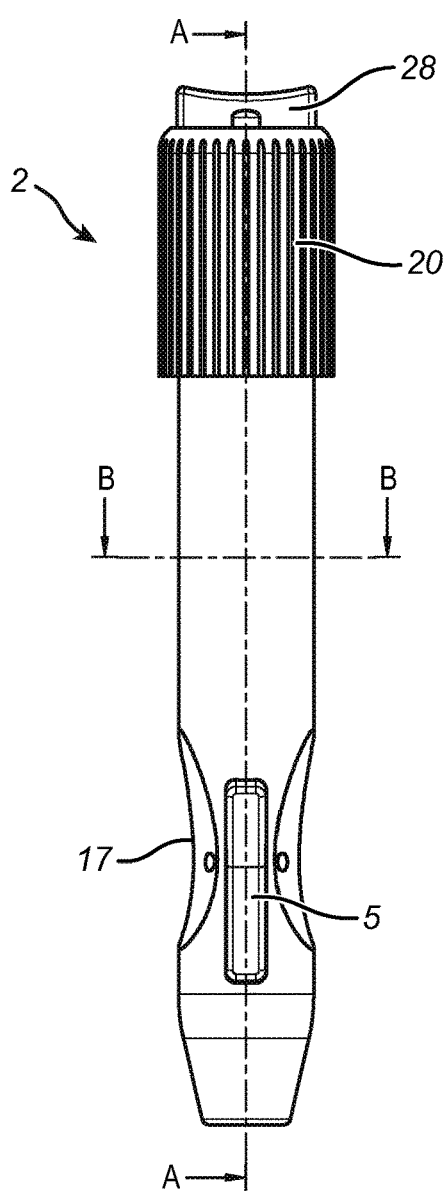
FIGS. 8A to 8C show a device according to an embodiment of the present invention in unlocked rest position.
Figure 8B:
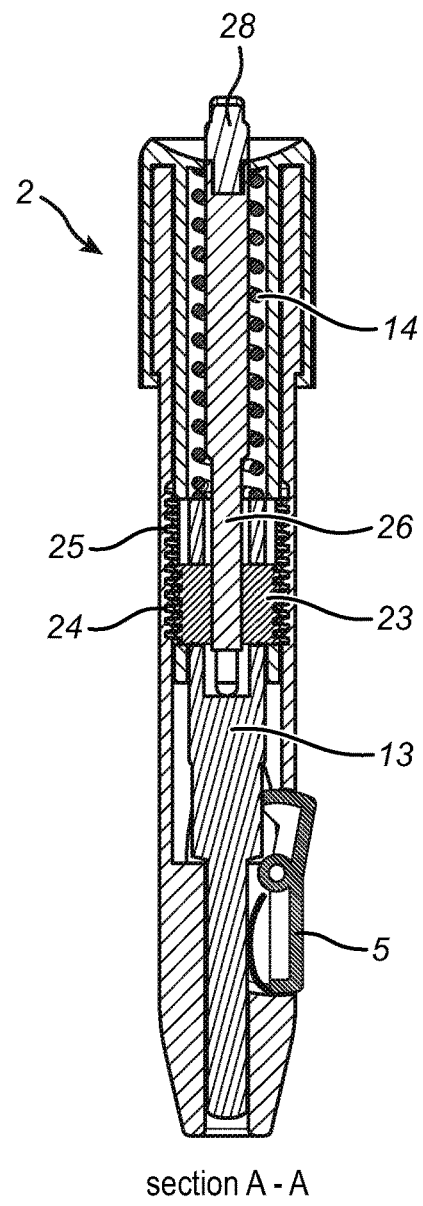
Figure 8C:
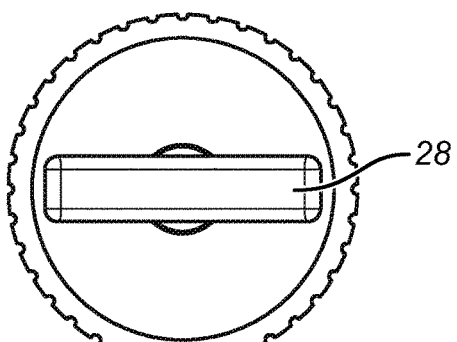

In an embodiment, the movable body 12 is not present in the cartridge 1, but the liquid will directly be pushed out through the force-displacing element 13. In an embodiment as illustrated in FIG. 6, the container can to this end be provided with a flexible closing member, that extends in the direction of the injection point 11 when the force-displacing element 13 moves downwards and comes into contact with the closing member 12. In this way, the liquid is pushed out of the cartridge 1 without the device itself coming into contact with this liquid. In another embodiment, a removable film is provided and the force-displacing element 12 thus comes into contact with the content of the cartridge 1.

FIG. 7A to FIG. 12 relate to an embodiment according to the present invention, in which the spring 14 of the spring mechanism is tightened by means of the presence of a thread element 23. This element 23 comprises at the outer side zones provided with a thread 24 or a toothed or grooved zone.

Figure 9A:
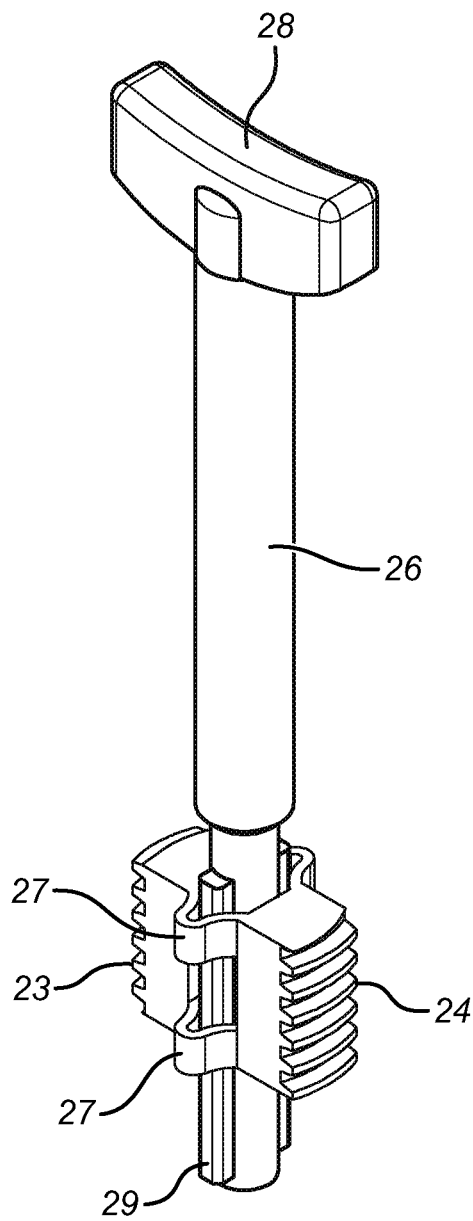
FIGS. 9A to 9D show a detailed view of the tensioning mechanism according to an embodiment of the present invention.
Figure 9B:
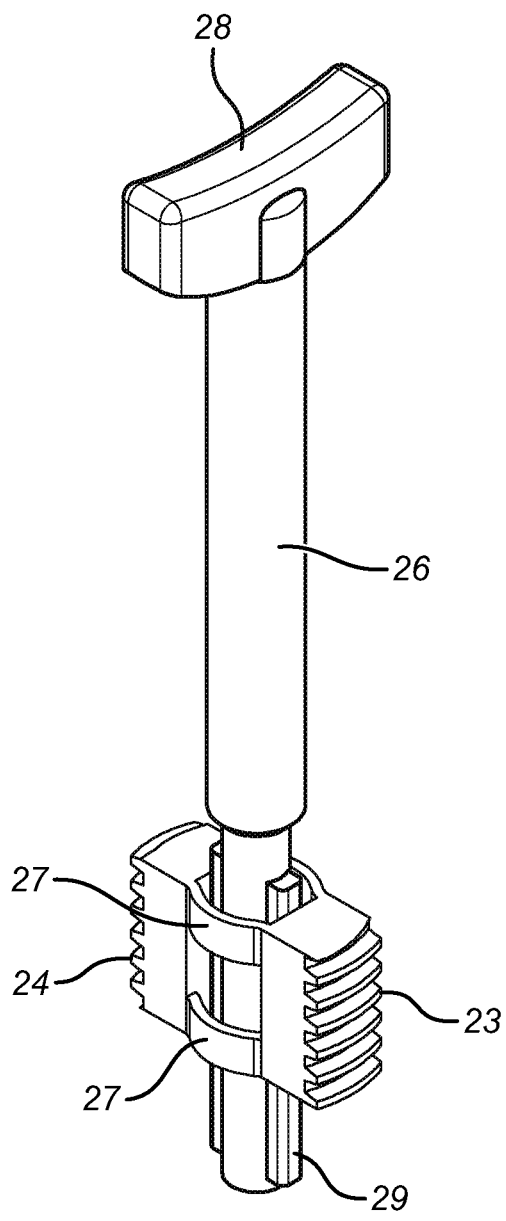
Figure 9C:
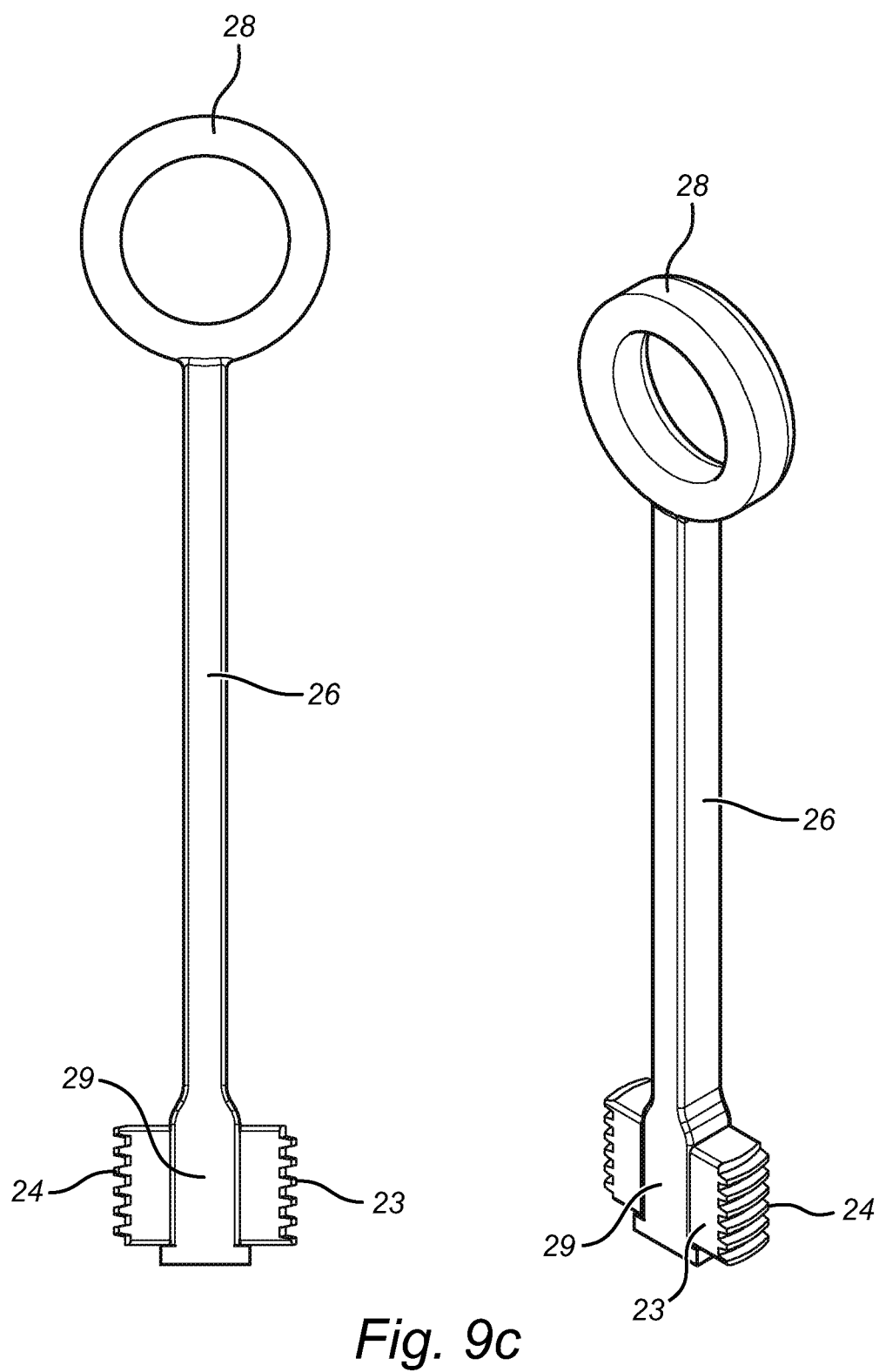
Figure 9D:
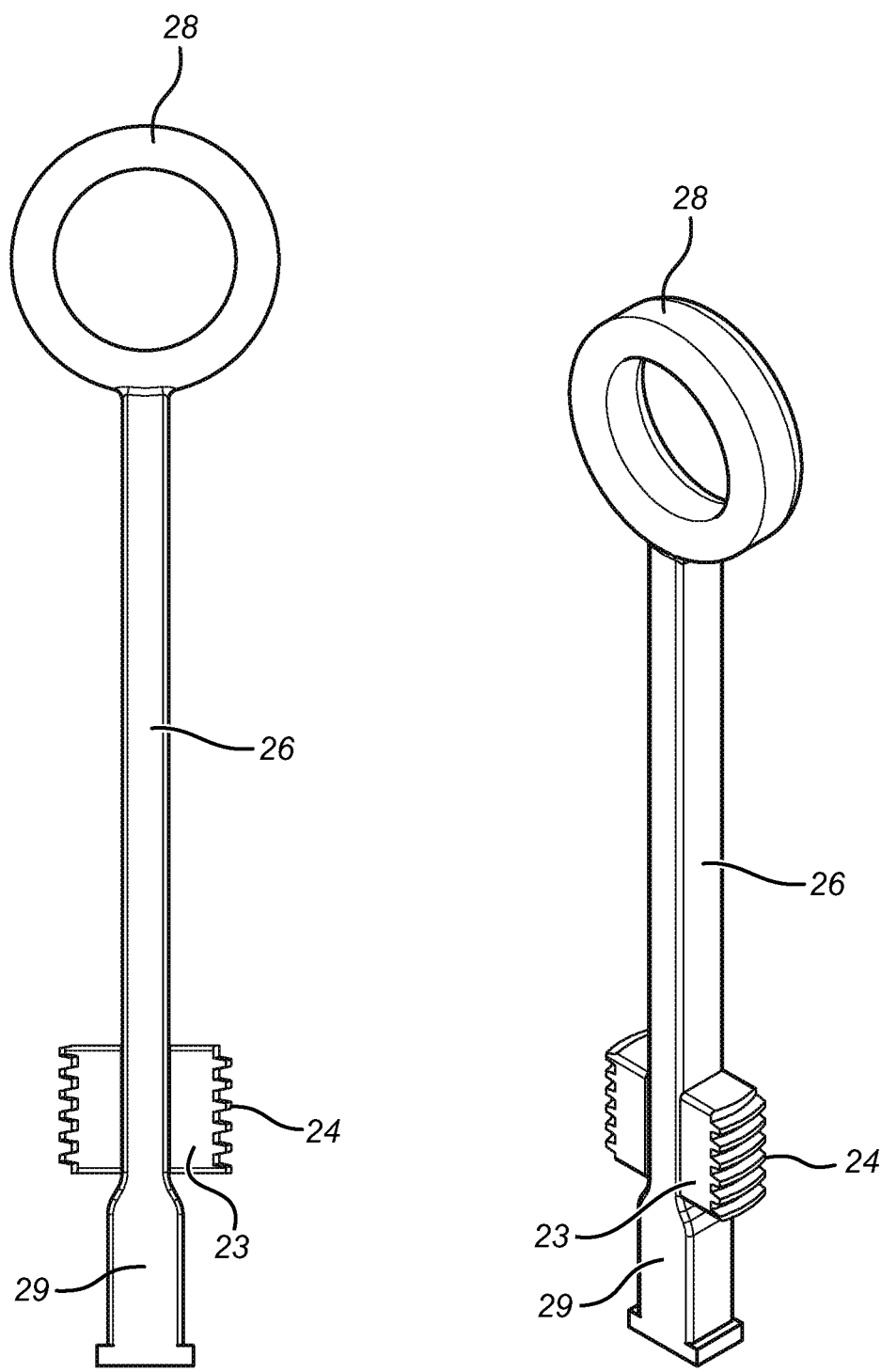

This zone 24 will preferably and under specific conditions correspond to a zone 25 provided internally in the casing. The thread element 23 is preferably made of a flexible polymer or a polymer with any deformable capacity. In particular and as illustrated in FIGS. 9A and 9B, the element 23 can be provided with lip-shaped structures 27, that make the diameter of the thread element 23 adaptable (broader or narrower within a particular range). FIGS. 9C and 9D show an alternative embodiment of the thread element 23, in which the lip-shaped structures are superfluous and the thread element 23 is composed of two subparts that are mutually connected, but in which the distance between the subparts can be adapted by means of a widening present at the rod-shaped element 26.

The variable opening of the thread element 23 or the distance between the two subparts of the element 23 can be adapted. To that end, the thread element 23 in the opening is provided with a rod-shaped element. By adjusting the position of the rod-shaped element 26 in the thread element, the opening of the thread element will or will not come into a 'wide' or 'narrow' position. This is the result of the width of the rod-shaped element that will respectively have a short and a long side. In the embodiment illustrated in the FIGS. 7A to 12, the rod-shaped element will be provided with a widening at two corresponding sides. This is also the case in the embodiment in FIGS. 9C and 9D. Adaptation of the position of the rod-shaped element 26 preferably occurs by means of a wing element 28 provided at the proximal end of the rod-shaped element and is possible by the user as it is visible at the outer side of the device.

When in the wide position, the thread element 23 will by means of its thread zone or grooved zone 24 be connected to the thread/grooved zone 25 of the casing. By further tensioning the turning mechanism, the element 23 will move upwards by means of the thread.

FIG. 7A shows an embodiment of a device 2 provided with a thread element 23. At the proximal end of the device 2, a wing element 28 is provided that enables the user to accumulate energy that is necessary for the use of the device. The device 2 is further also provided with a turning knob 20 that is also necessary for the tensioning of the spring mechanism. FIG. 7B is a cross-section of the device in FIG. 7A in initial, closed position. This is the position in which the device will be offered to the user. The device is in a safe mode and is not operable. The solution can thus not be evacuated unintentionally. This increases the safety of the device significantly.

In the closed position as illustrated in FIGS. 7B and 7C, the thread element 23 is in the lower position and cannot be raised. This is prevented because the rod-shaped element 26 keeps the opening of the thread element 23 in a small confirmation. This is illustrated in FIG. 7C which is a cross-section at the element 23 and the rod-shaped element 26. FIG. 9A shows a detailed view of the rod-shaped element 26 engaged with the thread element 23 in 'closed' position. The rod-shaped element is at two corresponding sides provided with a widening 29 that ensures the opening of the element 23 is in a wide (open) or narrow (closed) position. In closed position, as illustrated in FIGS. 7B-C and 9A, the widenings 29 will be faced to the lip-shaped structures 27 of the element 23. The element 23 with a narrow diameter will not be able to engage in a correct way with the thread zone 25 of the casing, the spring cannot be tightened. The device is not in an operable condition.

FIGS. 8A to 8C and FIG. 9B show the device 1 in unlocked position. Hereby, the rod-shaped element 26 will by means of the wing element 28 be turned a quarter of a turn. Hereby, the widenings 29 will be faced away of the lip-shaped structures, but towards the thread zones 24 of the element 23. The diameter of the element 23 thus increases and the zone 24 of the element will be able to be engaged with the zone 25 of the casing.

Figure 10:
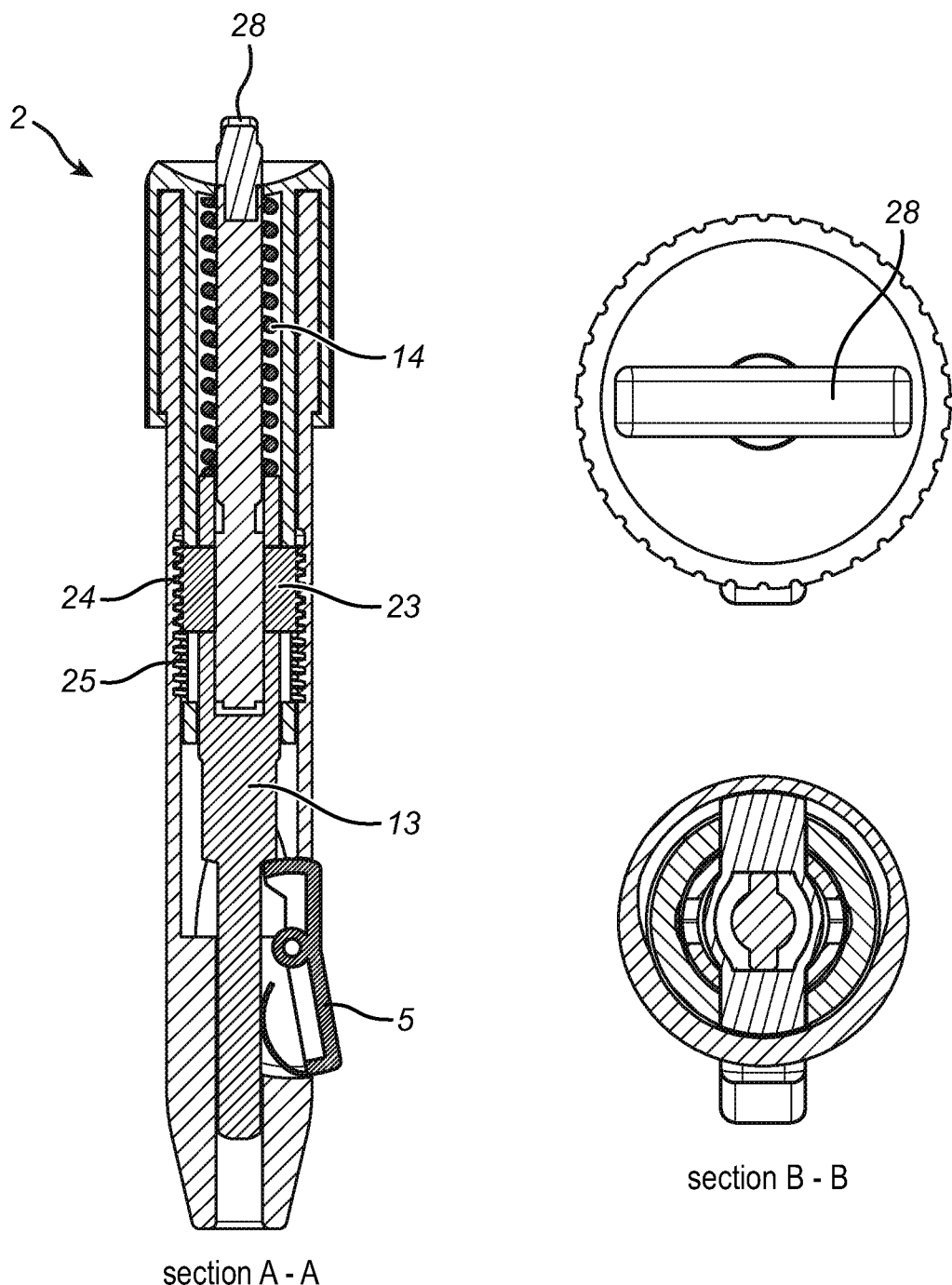
FIG. 10 shows a device according to an embodiment of the present invention in locked launching condition.
Figure 11:
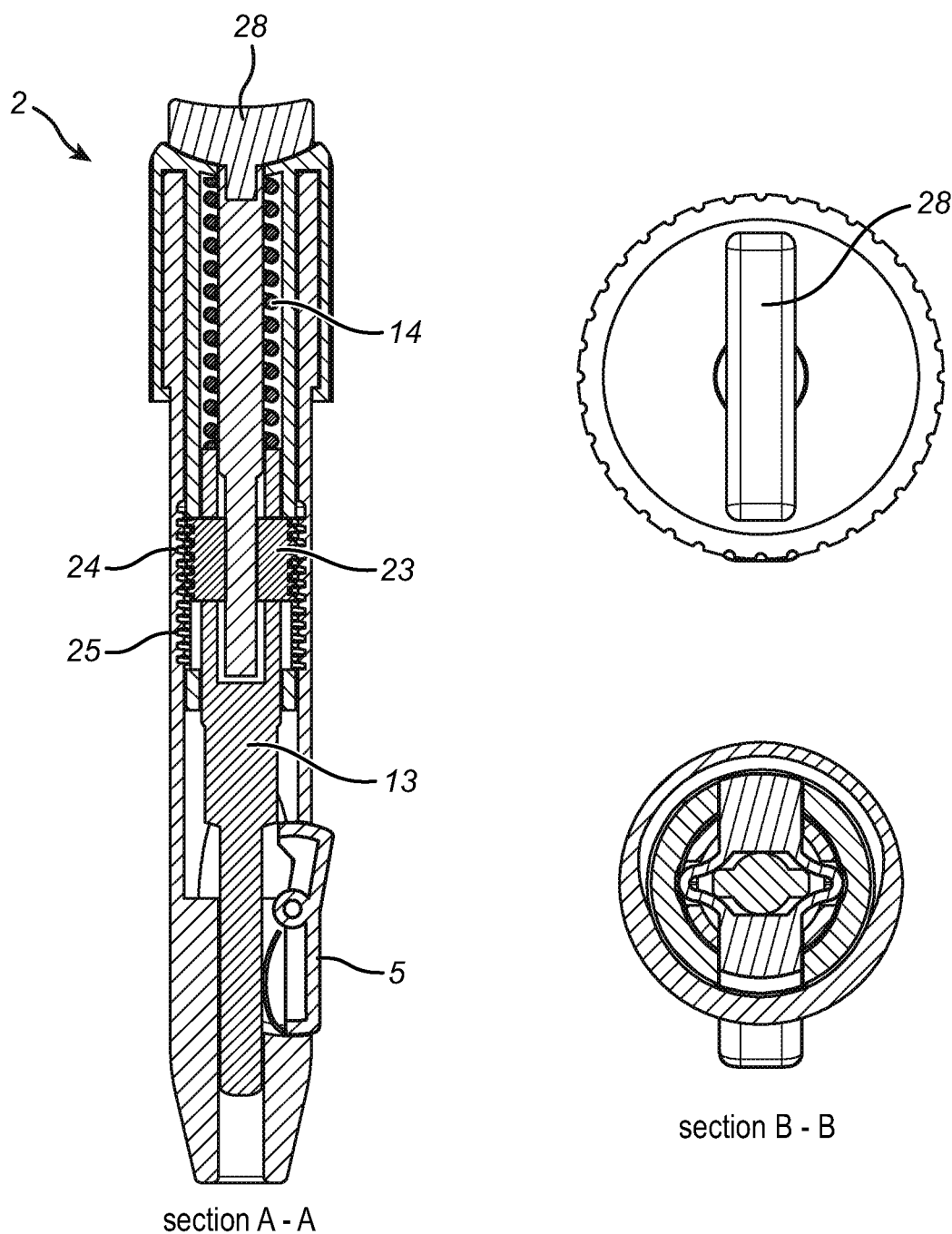
FIG. 11 shows a device according to an embodiment of the present invention in unlocked launching condition.

By tensioning the turning knob 20 and/or the wing element 28, the thread element 23 will move upwards along the thread 25 of the casing and the spring 14 will thus be pushed in. The necessary force will thus be generated. FIG. 10 shows a cross-section of the device, in which the thread element 23 is in the highest position. The force-displacing element 13 will as a result also be raised in the casing at the position where it is connected to the spring 14.

Optionally and as a safety measure, the release mechanism 5 can be locked in the position as shown in FIG. 10. In this way, the device cannot be activated accidently (for example when it has not yet been positioned correctly). Moreover, the user receives in this way the indication that the spring is sufficiently tightened. The release mechanism 5 can be locked by a second spring that is provided in the device.

The device can subsequently be placed specifically at the location on the skin where the liquid should be administrated. Subsequently, the device has to be unlocked. This is realized by turning the wing element 28 a quarter turn, preferably in counter-clockwise. As a result, the release mechanism 5 will again be unlocked, the rod-shaped element will again place the diameter of the thread element in a wide position and the device is ready for use, i.e. the release of the fluid (see FIG. 11).

Figure 12:
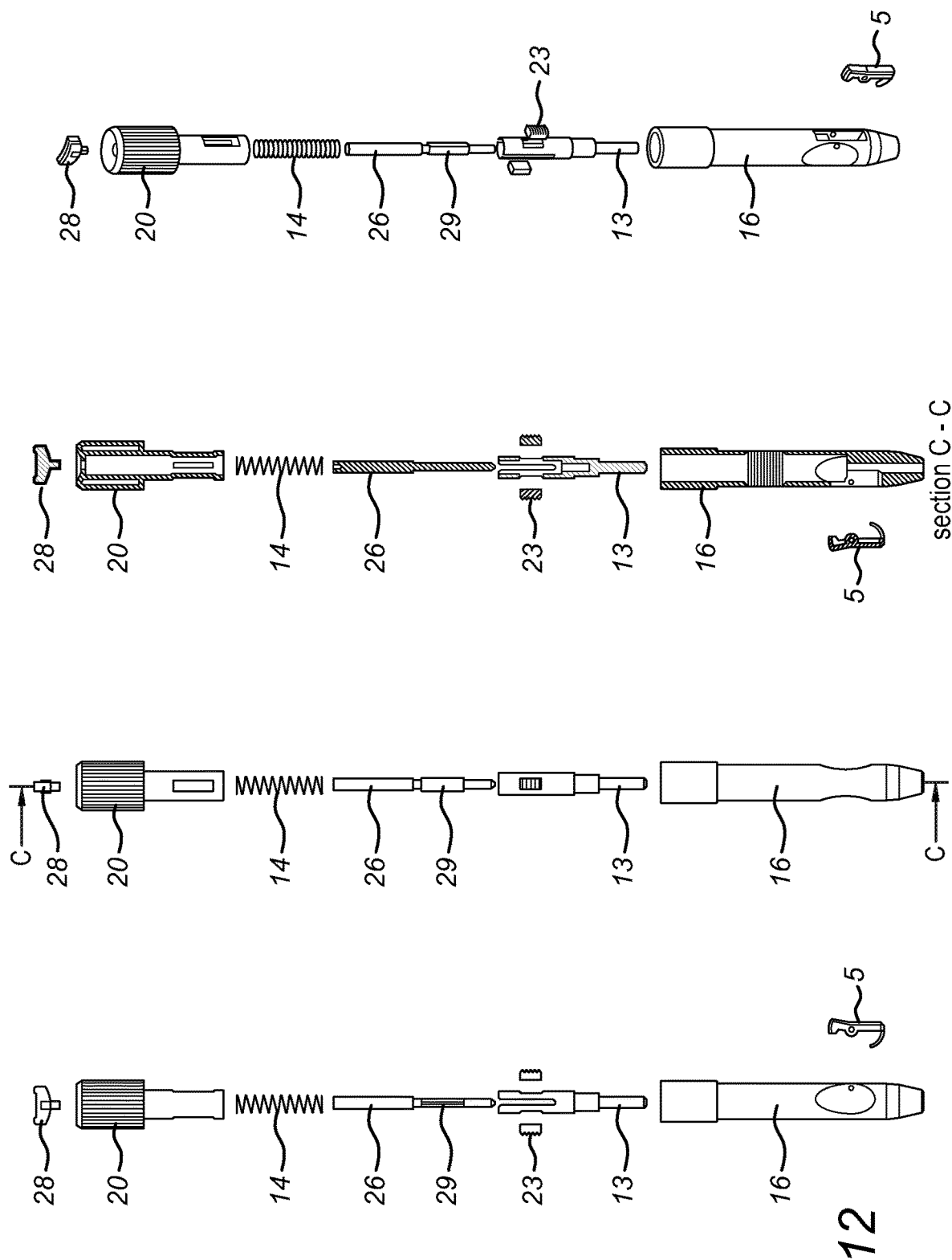
FIG. 12 shows an embodiment of a device according to the present invention, in which parts are shown separately.

FIG. 12 shows an embodiment of a device according to the present invention, in which parts are shown separately.

Figure 13:
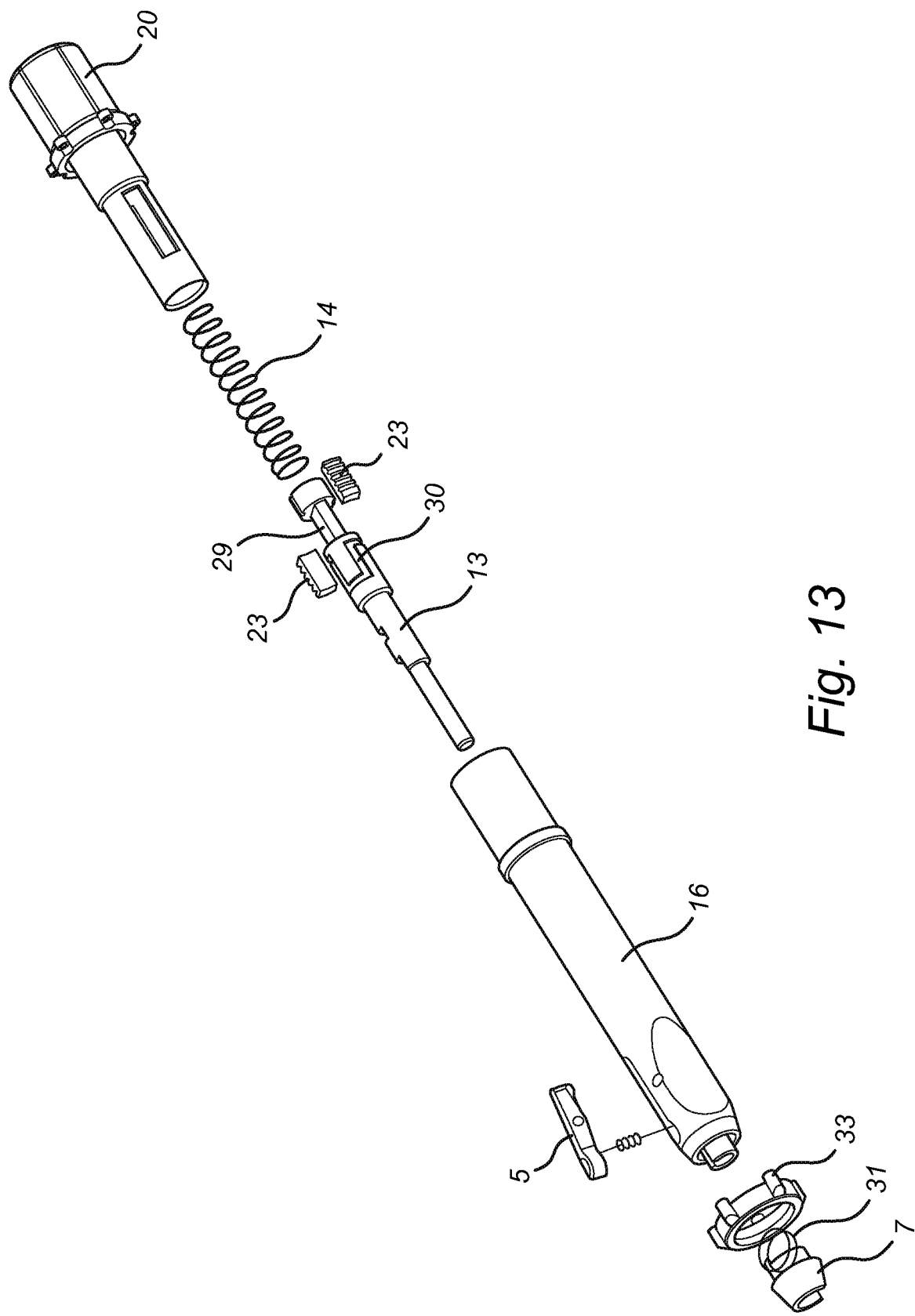
FIG. 13 shows another embodiment of a device according to the present invention, in which parts are illustrated separately.

FIG. 13 illustrates another embodiment of the device according to the present invention. The force-displacing element 13 comprises a guiding path 30, adjustably connected to the casing and appropriate for guiding the completion of the different phases in the tensioning process. The rod-shaped element, that determines the diameter of the opening of the thread elements by means of a widening 29, is part of the force-displacing element in this embodiment. At the distal end of the casing 16, a cartridge receiving means 7 comprising a recess is provided. The profile is attached to the casing by means of a mounting ring 33. Between the cartridge receiving means and the mounting ring 33, a spring 31 is placed, appropriate for pushing in the cartridge receiving means against the casing. In this way, the user can place the injection device in a user-friendly way on the targeted skin. In a preferred embodiment, the spring system 31 comprises a safety mechanism, as a result of which the injection device cannot be unloaded if the spring system is not pushed in.

Figure 14:
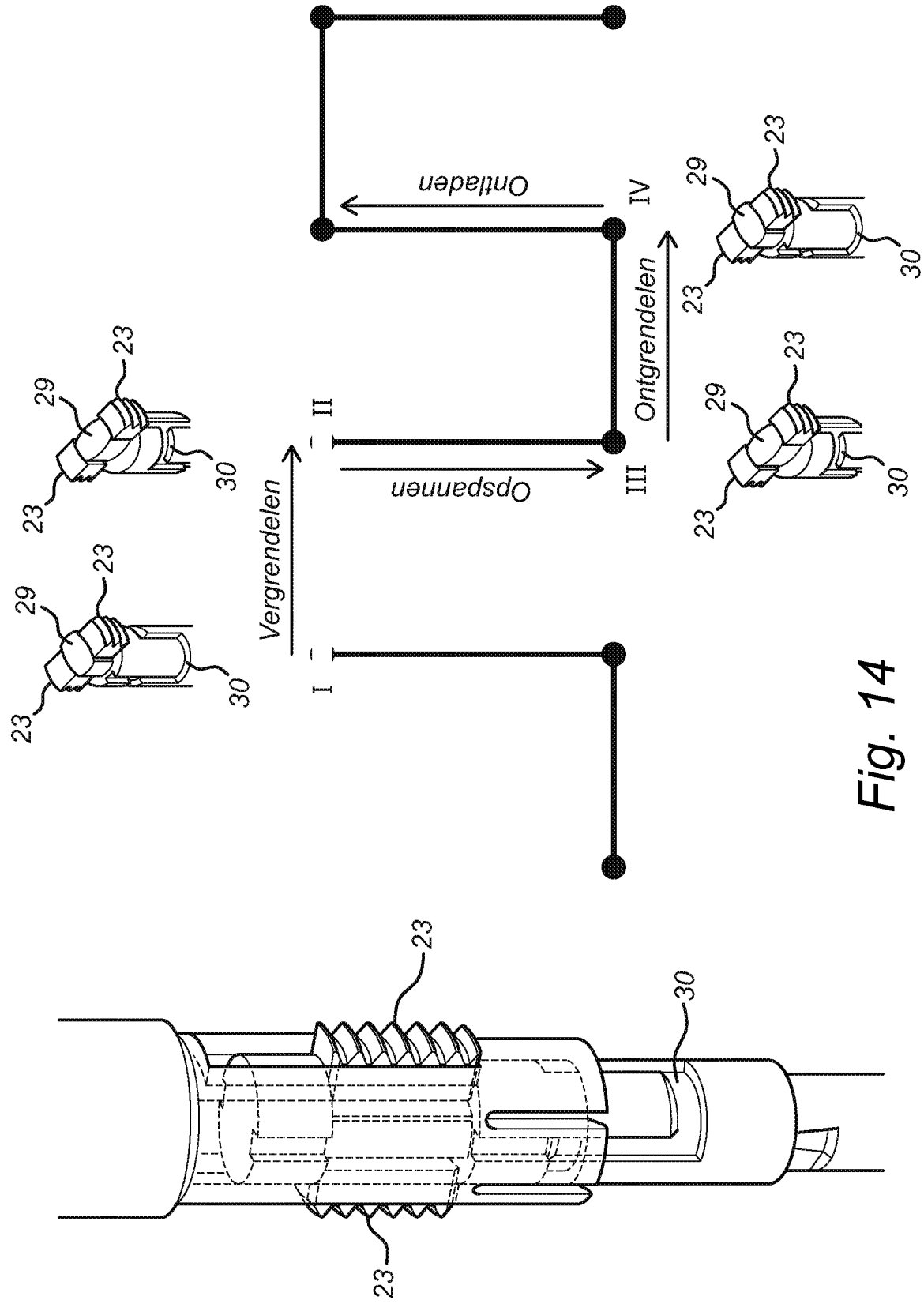
FIG. 14 shows an embodiment of a guiding path, in which the position of the thread elements is discussed in detail during the different phases of the tensioning process.
Figure 15A:
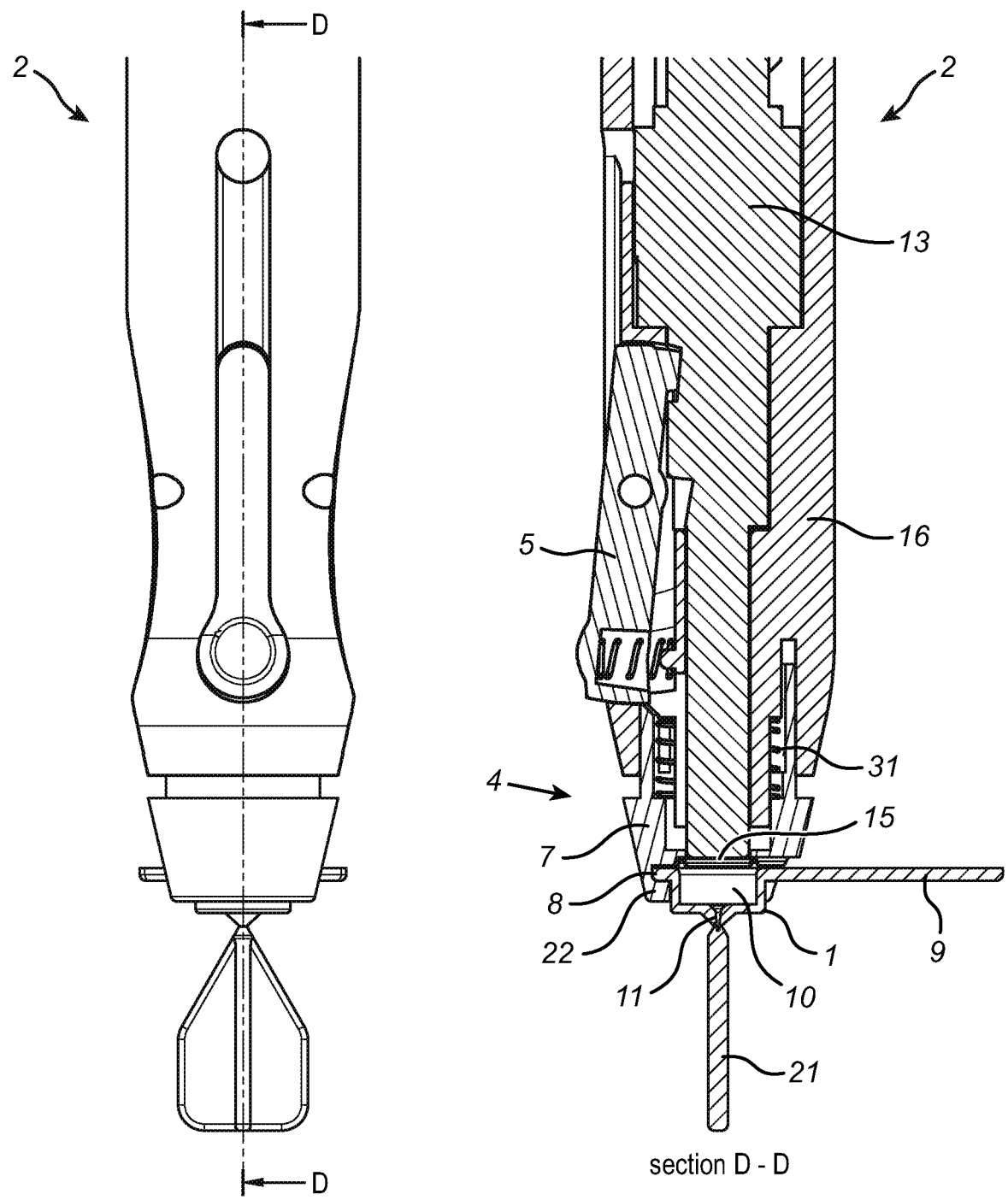
FIG. 15A to 15D show an embodiment of a device according to the present invention, in which a second spring mechanism is provided in the tip of the device.
Figure 15B:
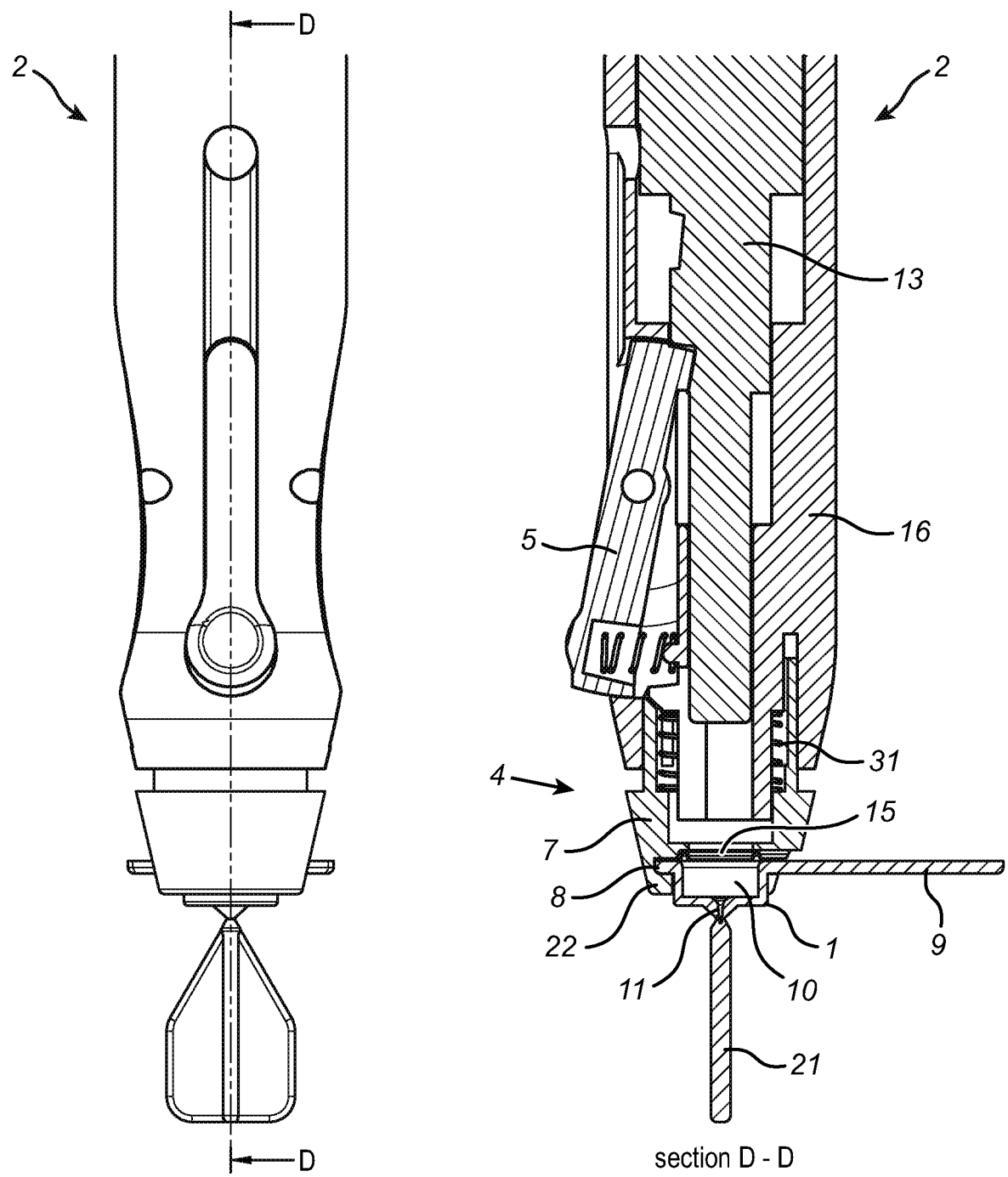
Figure 15C:
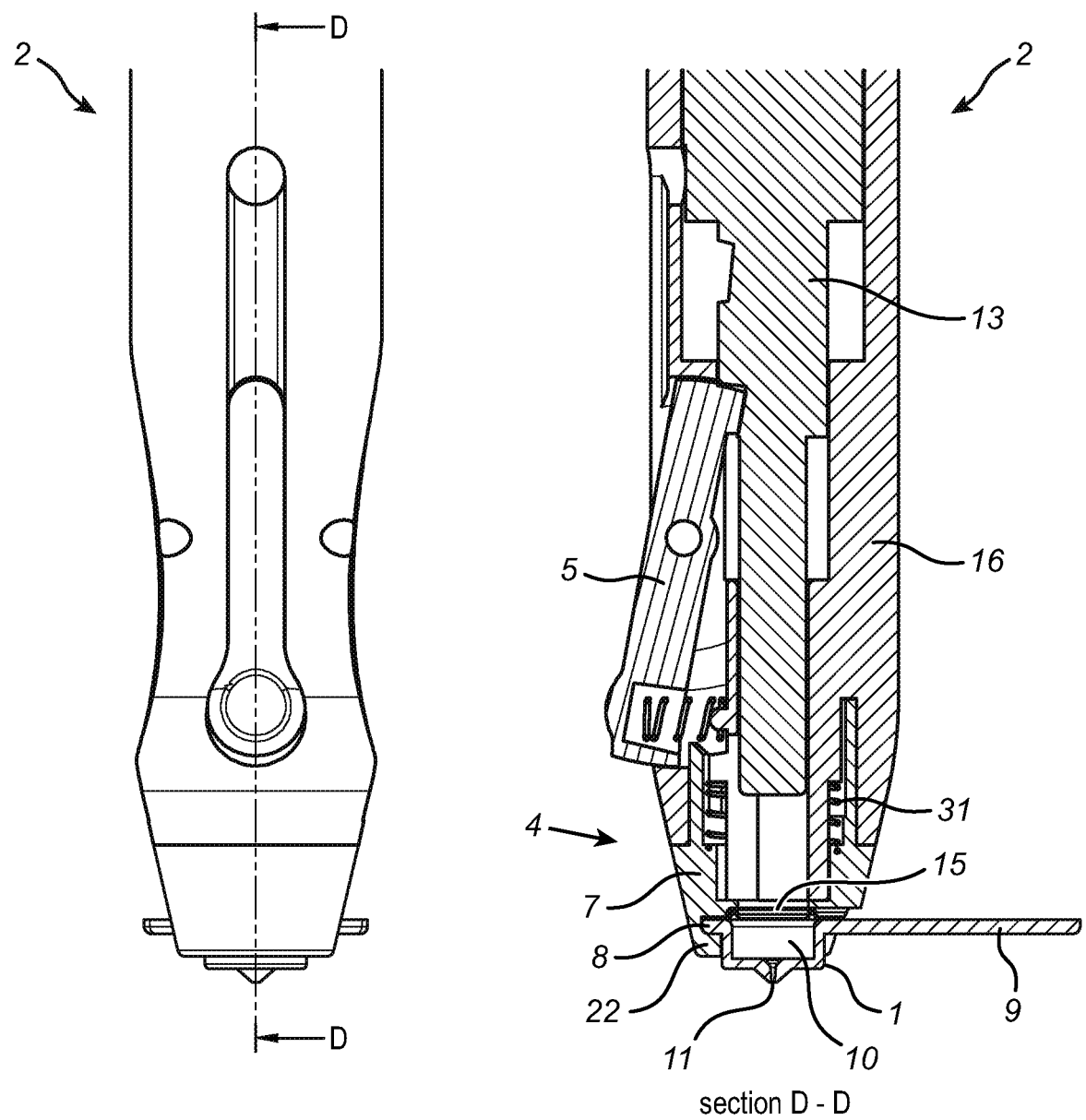
Figure 15D:
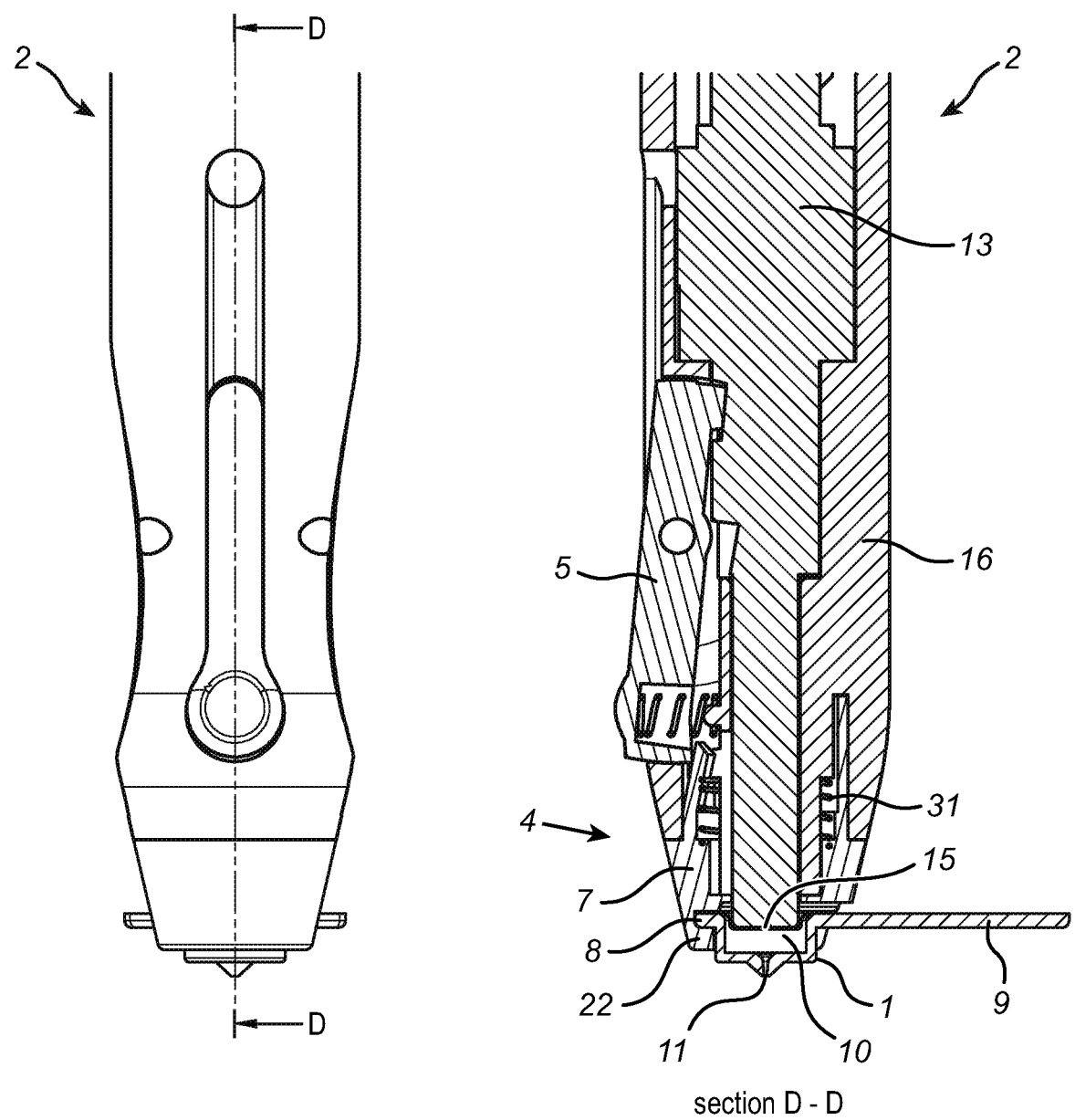

FIG. 14 focuses on an embodiment of the guiding path 30 provided in the force-displacing element. In this embodiment, the guiding path is merlon-shaped, as a result of which the different tensioning phases can be completed by simple turning movements. The start position is indicated on the merlon-shaped line as step I. In step I, the main axis of the (in the present case elliptical) widening is perpendicular to the position of the thread elements 23. By turning the turning knob (1) 90°, the thread elements 23 are positioned in a wide position, in which the main axis of the widening 29 is positioned in the direction of the thread elements (step II). In the wide position, the thread elements 23 will by means of its thread zone or grooved zone 24 be configured in the internal thread/grooved zone 25 of the casing. When the turning knob is further turned, the merlon-shaped guiding path 30 prevents a horizontal movement, only a vertical movement is possible. As a result, the thread elements remain in the wide position, so that the thread elements (and thus also the force-displacing element) are raised by means of the thread. A user must turn the turning knob e.g. 5 complete turns to fully tighten the injection device and to go through the complete vertical length of the guiding path 30 till position III. In this position, the guiding path 30 again allows a horizontal movement. When the turning knob is further turned, the thread elements 23 are unlocked, i.e. the main axis of the widening 29 is again positioned perpendicular onto the position of the thread elements. The injection device is now tightened and ready for delivering under pressure a chemical composition. In a preferred embodiment, the cartridge can be shifted into the recess of the cartridge receiving means before or after loading the injection device. By means of a pressure on the release mechanism, the force-displacing element moves in the distal direction and pushes out the chemical composition under pressure in the direction of the skin. After releasing, the injection device is again positioned as in position I, as a result of which the injection device can again be used by completing the same steps, as described above.

In FIG. 15(*a*-*d*), a cross-section of another embodiment of an injection device 2 is shown, provided with a spring mechanism 31 at the tip (distal end 4) of the injection device. The peripheral edge 8 of a cartridge 1 is positioned in the recess/lip structure 22 of the cartridge receiving means 7. In FIG. 15*a*, a force-displacing element is in released condition (cf. position I in FIG. 14). The spring mechanism 31 in the tip is also in released condition, as a result of which the receiving means 7 are not pushed against the casing 16. The distal end of the force-displacing element 13 is positioned at the closing means 15 of the cartridge. The tip of the injection device can preferably only be pushed in when the pen is in tightened position. In this way, the chemical composition cannot be pushed out of the cartridge by the force-displacing element if the tip is pushed against the casing. In this embodiment, the injection device can be released without positioning the tip against the casing. Because the spring mechanism 31 is between the tip and the casing/body of the injection device, the force-displacing element doesn't come into contact with the closing means 15 and the chemical composition is not pushed out if the device was not placed against the skin and the spring mechanism 31 was pushed in. In FIG. 15*b*, the injection device is loaded, in which the release mechanism 5 is hooked/clipped into a recess of the force-displacing element. The spring mechanism 31 in the tip of the casing is still in released position, in which the distal and of the casing and the proximal end of the cartridge do not touch each other. In FIG. 15*c*, the closing means 21 at the distal end of the cartridge was removed. The injection device is in a loaded condition, in which the spring mechanism 31 in the tip of the injection device is pushed in by placing the tip on the skin of the user. In FIG. 15*d*, the position of the injection device is shown after the release mechanism 5 was pushed in. The force-displacing element 13 pushed in the flexible closing means 15 of the cartridge, as a result of which the composition in the container was pushed out through the injection point 11. A user can then remove the injection device from the skin, as a result of which the spring mechanism 31 will again release. The cartridge, provided with a handle at the proximal end, can safely be removed from the injection device, because the injection point is positioned at the distal end. By providing this handle (at the opposite side of the injection point), it is avoided that rests of the chemical composition that have not been absorbed by the skin to treat, stay behind on the hands of a user.

Such an embodiment allows to operate the device according to the invention in a safely manner and this by manually generating a sufficient force so that the fluid is brought into or on the skin at a high pressure.

Example 1

Acid-Based Compositions

The present invention can use the following acid-based compositions; these examples are not limitative for the present invention (proportions expressed in (w/w)):

Composition 1

40% TCA, 4% carboxymethylcellulose and $H_2O$ at pH 2

Composition 2

40% TCA, 4% carboxymethylcellulose, 2% salicyclic acid and $H_2O$ at pH 3

Composition 3

40% TCA, 1% carbopol and $H_2O$

Composition 4

50% monochloroacetic acid and $H_2O$

Composition 5

70% citric acid, glycerol, lemon oil, $H_2O$

Composition 6

167 mg/g salicyclic acid and 167 mg/g lactic acid in collodium composition

Composition 7

40% TCA, 2% carbopol, 12% glycerine and $H_2O$ to 100% (pH 2, viscosity 8000)

Composition 8

2% salicyclic acid, 2% carbopol, 12% glycerine and $H_2O$ to 100% (pH 3, viscosity 8000)

Composition 9

40% TCA, 2% salicyclic acid, 2% carbopol, 12% glycerine and $H_2O$ to 100% (pH 2, viscosity 8000)

Composition 10

40% TCA, 1.5% carbopol and $H_2O$ to 100% (pH<2, viscosity 6000-8000)

Composition 11

20% TCA, 1.75% carbopol and $H_2O$ to 100% (pH<2, viscosity 3000-4000)

Composition 12

20% TCA, 2% carbopol and $H_2O$ to 100% (pH<2, viscosity 4000-6000)

Composition 13

30% TCA, 2% hydroxypropyl cellulose, 4% castor oil, 20% methanol, aceton to 100% (pH 2, viscosity 3000)

Composition 14

2% salicyclic acid, 2% hydroxypropyl cellulose, 4% castor oil, 20% methanol, aceton to 100% (pH 3, viscosity 3000)

Composition 15

30% TCA, 2% salicyclic acid, 2% hydroxypropyl cellulose, 4% castor oil, 20% methanol, aceton to 100% (pH 2, viscosity 3000)

Composition 16

3% TCA, 1% sodium gluconate, 0.2% sodium benzoate, 0.2% potassium sorbate, 4.5% Eusolex® T-oleo, 1.5% Eusolex®4360, 1% Eusolex®2292, 5% PEG-40, 6% glycerine, 5% carboxymethyl cellulose, $H_2O$ to 100% (pH 4, viscosity 6000 to 7000)

Composition 17

3% TCA, 1% sodium gluconate, 0.2% sodium benzoate, 0.2% potassium sorbate, 3% glycerine, 2.5% carboxymethyl cellulose, $H_2O$ to 100% (pH 3, viscosity 6000 to 8000)

Composition 18

2% TCA, 0.4% sodium gluconate, 0.2% sodium benzoate, 0.2% potassium sorbate, 5% glycerine, 2.5% carbopol, $H_2O$ to 100% (pH 2, viscosity 7000 to 10000)

Composition 19

0.4% TCA, 5% olive leaf *Lactobacillus* extract, 5.6% glycerien, 0.1% allantoin, 1% urea, 1.5% dimethyl isosorbide, 2.6% sodium hydroxide, 0.9% carbopol, 1% D-panthenol, 0.2% potassium sorbate, 0.4% xanthum gum, 0.02% sodium benzoate, $H_2O$ to 100% (pH 4.5-5.5, viscosity 4000 to 8000)

REFERENCE FIGURES

1: cartridge
2: injection device
3: proximal end device
4: distal end device
5: release mechanism
6: tensioning mechanism
7: cartridge receiving means (recess)
8: peripheral edge
9: handle
10: container
11: injection point
12: movable body
13: force-displacing element
14: spring
15: closing means
16 casing
17: grip
18: composition
19: strip
20: turning knob
21: closing means
22: lip structure
23: thread element
24: thread zone/grooved zone of thread element
25: thread zone/grooved zone of casing
26: rod-shaped element
27: lip-shaped structure
28: wing element
29: widening
30: guiding path
31: spring at tip of injection device
33: mounting ring

The invention claimed is:

1. A kit for applying a liquid composition on or in the skin, the kit comprising:
   an injection device that comprises
   a casing having a thread, in which the casing is provided at a distal end with a receiver arranged to receive a cartridge,
   a thread element arranged to engage said thread, and
   a force-displacing element that is adjustable along a longitudinal axis of the injection device by a spring mechanism; and
   one or more cartridges provided with a container for receiving a liquid composition,
   wherein the force-displacing element comprises
   a widening that is arranged to move the thread element from a narrow position to a wide position in which the thread element engages said thread, and
   a guiding path that is adjustably coupled to the casing.

2. The kit according to claim 1, characterized in that the force-displacing element comprises a rod-shaped element that is provided with the widening.

3. The kit according to claim 1, characterized in that the guiding path is merlon-shaped.

4. The kit according to claim 1, characterized in that the receiver comprises a recess at a distal end of the injection device.

5. The kit according to claim 1, characterized in that the cartridge comprises a distal end and a proximal end and that the distal end of the cartridge comprises an injection tip.

6. The kit according to claim 4, characterized in that the cartridge comprises a peripheral edge that is configured to be received in the recess.

7. The kit according to claim 6, characterized in that the peripheral edge is symmetrical or asymmetrical.

8. The kit according to claim 6, characterized in that the peripheral edge is provided at a proximal end of the cartridge.

9. The kit according to claim 1, characterized in that the casing of the injection device is provided at a proximal end with a tensioning system for the spring mechanism.

10. The kit according to claim 1, characterized in that the injection device comprises a second spring mechanism provided between the receiver and a distal end of the casing.

11. The kit according to claim 1, characterized in that the casing is externally provided with a user-operable releasing mechanism configured to release the spring mechanism.

12. The kit according to claim 1, characterized in that a distal end of the force-displacing element is moveable between a position within the casing and a position at or past the distal end of the injection device.

13. The kit according claim 1, characterized in that the cartridge comprises a closing means at a proximal end and a distal end, in which at least one of (i) the closing means at the proximal end is breakable or flexible and (ii) the closing means at the distal end is removable.

14. The kit according to claim 1, characterized in that at least one of the injection device and the cartridge is at least partially manufactured of an acid-resistant polymer.

15. The kit according to claim 14, characterized in that the acid-resistant polymer is chosen from a group comprising polyphenylene sulfide, polyoxymethylene, polypropylene, polyethylene, ultra-high molecular weight polyethylene (UHMW-PE), co-polymers of acetal, ethylene vinyl acetate (EVA), polyethylene terephthalate, thermoplastic polyester elastomers (TPE-ET), polycyclohexylenedimethylene terephthalates (PCT), polybutylene terephthalates (PBT), halogen-free liquid crystal polymers (LCP), and PC-ABS.

16. The kit according to claim 1, characterized in that the container comprises a liquid composition, in which the liquid composition comprises a therapeutically effective amount of acid selected from a group comprising fruit acids (AHAs), acetic acid, trichloroacetic acid, dichloroacetic acid, hydrochloric acid, formic acid, kojic acid, azelaic acid, phosphoric acid, thioglycolic acid, retinoic acid, salts, phenols, and esters.

17. A kit for applying a liquid composition on or in the skin, the kit comprising:
an injection device arranged to receive a cartridge having a container comprising a liquid composition, the injection device comprising
a casing having a thread,
a thread element arranged to engage said thread, and
a force-displacing element that is adjustable along a longitudinal axis of the injection device by a spring mechanism,
wherein the force-displacing element comprises
a widening that is arranged to move the thread element from a narrow position to a wide position in which the thread element engages said thread, and
a guiding path that is adjustably coupled to the casing.

18. The kit according to claim 17, characterized in that the guiding path is merlon-shaped.

* * * * *